United States Patent
Elazar et al.

(10) Patent No.: US 10,687,917 B2
(45) Date of Patent: Jun. 23, 2020

(54) USING IMMERSIVE PHOTOGRAPHS TO GUIDE PLACEMENT OF ORTHODONTIC BRACKETS, AND APPLICATIONS THEREOF

(71) Applicant: Dental SmartMirror, Inc., Chicago, IL (US)

(72) Inventors: Gidon Oded Elazar, Cohav Yair (IL); Dan Zidkiahu Harkabi, Moshav Lachish (IL); Joshua Israel Wachspress, Modi'in (IL); Yael Miriam Harkabi, Moshav Lachish (IL)

(73) Assignee: Dental SmartMirror, Inc., Tel Aviv-Jaffa (IL)

( * ) Notice: Subject to any disclaimer, the term of this patent is extended or adjusted under 35 U.S.C. 154(b) by 8 days.

(21) Appl. No.: 15/650,068

(22) Filed: Jul. 14, 2017

(65) Prior Publication Data
US 2019/0015177 A1    Jan. 17, 2019

(51) Int. Cl.
| | | |
|---|---|---|
| A61C 7/14 | (2006.01) | |
| A61C 7/00 | (2006.01) | |
| G06F 19/00 | (2018.01) | |
| A61C 9/00 | (2006.01) | |
| G16H 30/40 | (2018.01) | |
| G16H 40/60 | (2018.01) | |
| G16H 20/40 | (2018.01) | |
| G16H 50/50 | (2018.01) | |

(52) U.S. Cl.
CPC ............. *A61C 7/146* (2013.01); *A61C 7/002* (2013.01); *A61C 9/0046* (2013.01); *A61C 9/0053* (2013.01); *G06F 19/321* (2013.01); *G16H 20/40* (2018.01); *G16H 30/40* (2018.01); *G16H 40/60* (2018.01); *A61C 9/0006* (2013.01); *G16H 50/50* (2018.01)

(58) Field of Classification Search
CPC .......... A61C 7/002; A61C 7/146; A61C 7/00; A61C 13/0004; A61C 9/0053; A61C 3/00
See application file for complete search history.

(56) References Cited

U.S. PATENT DOCUMENTS

| | | | | |
|---|---|---|---|---|
| 6,334,772 B1 * | 1/2002 | Taub | ...................... | A61C 7/146 433/24 |
| 6,632,089 B2 * | 10/2003 | Rubbert | ................... | A61C 7/00 433/24 |
| 6,648,640 B2 * | 11/2003 | Rubbert | ................... | A61C 7/00 433/24 |

(Continued)

OTHER PUBLICATIONS

Notification of Transmittal of the International Search Report and the Written Opinion of the International Searching Authority, or the Declaration issued in International Application PCT/US2018/040761, dated Sep. 27, 2018, 12 pages.

*Primary Examiner* — Ralph A Lewis

(57) ABSTRACT

In an embodiment, an input indicating a location selected by a health care professional on an image rendered with respect to a viewport mapped onto an immersive photographic model of a patient's mouth to indicate a position to place an orthodontic bracket on a patient's tooth is received. A ray is extended from a focal point of the viewport at a direction determined based on the input. An intersection of the ray in a three-dimensional space is determined. The intersection indicates a position to place the orthodontic bracket on the patient's tooth.

15 Claims, 15 Drawing Sheets

(56) References Cited

U.S. PATENT DOCUMENTS

| | | | | |
|---|---|---|---|---|
| 6,971,873 B2* | 12/2005 | Sachdeva | ............... | A61C 7/00 |
| | | | | 433/24 |
| 7,027,642 B2* | 4/2006 | Rubbert | ............... | A61C 7/00 |
| | | | | 382/154 |
| 7,080,979 B2* | 7/2006 | Rubbert | ............... | G16H 50/50 |
| | | | | 433/24 |
| 2003/0027098 A1 | 2/2003 | Manemann et al. | | |
| 2007/0099146 A1 | 5/2007 | Reising | | |

* cited by examiner

USING IMMERSIVE PHOTOGRAPHS TO GUIDE PLACEMENT OF ORTHODONTIC BRACKETS, AND APPLICATIONS THEREOF

BACKGROUND

Field

This field is generally related to placement of orthodontic brackets.

Related Art

Dental Digital 3D Scanning

In dentistry, including orthodontics, multiple procedures exist that require generating a three-dimensional (3D) model of a patient's mouth. At present, many of these models are created using physical impression materials which are then used to generate a physical plaster model. Recently, technologies and products have emerged for the creation of a digital representation of the 3D modeling, the models commonly called "digital impressions."

A digital impression is a synthetic representation of the surfaces within a patient's mouth, and mainly the teeth, within a three-dimensional space. The target of such models is, generally, for usage by computer programs to process. For example, a digital impression may be used for a computer to design the dimension of a missing tooth in a patient's mouth, thereafter 3D printing it for creating a prosthesis. Or, for example, a doctor can use a synthetic 3D model to measure distances between teeth, with the achieved measurements accuracy comparable to the accuracy of the model, which sometimes surpasses the accuracy of measurements taken directly on the patient's mouth. In the field of orthodontics such a model can aid in the diagnostic process, and further be used for calculating the end arch form, for designing and fabricating orthodontic appliances such as retainers, and for making decisions for bracket placement.

A 3D model can also be used to present a rendering of a patient's mouth. To achieve photo-realistic quality, actual images of the same teeth can be used to extract texture and apply it to the synthetic rendering.

Immersive Photography

Immersive photography, also referred to as 360 photography or virtual reality (VR), is increasingly being applied to various fields, mostly in the entertainment industry, such as the introduction of 360 videos to Google's YouTube, or Sony's VR games for its PlayStation video game console. But also increasingly to other fields, for example ESPN 360 sports journalism, and the contemporary effort by Facebook to promote the creation of immersive content by publishing its Surround 360 system.

An observer may only be observing a section of the immersive photograph. The section depends on a point of viewing, or perspective, selected by the observer. The observer may select another point of view to observe a different section, much like persons use their eyes to watch what is in front of them, but can turn around to observe what is behind. Since people are used to viewing the world around in such a manner, the immersive photography increases the appearance of reality, which by itself provides a sense of a 3D scene, despite the fact that the immersive photograph is a result of stitching a series of two-dimensional images.

One technique to capture an immersive photograph is using a multi-camera device. The cameras are positioned such that they are at an angle to each other, covering an area around a point. The various cameras synchronously capture images, thereafter the images are stitched, so that a continuous photo is achieved. To view a perspective of the immersive photograph, software allows the selection of the angle of rotation around the point. The software presents the appropriate section of the photograph visible from the selected angle.

In an immersive video, perspectives are selected around a point that might be in motion, corresponding to the motion of the camera while the video was captured.

Stereo Photography and Stereo Immersive Photography

A stereo photograph is composed of two images having substantially the same visual content, and captured substantially toward the same direction, much like a person's eyes views the scene ahead. To observe a stereo photograph, the visual information is thereafter separate to the respective eyes, one image intended to be observed by a person's right eye and the other by the left eye. The human mind combines the images to provide a three dimensional sense that includes depth.

Stereo photographs and videos are used in various fields, for example in entertainment, where the so-called 3D movies, which allows an audience to watch a stereo video, while the provided glasses split the visual content to be views by the left eye and right eye appropriately. Some television vendors have produced 3D-TVs, and some have been able to produce screens that show a different image to each of the eyes without requiring glasses, for example by using techniques such as parallax-barrier.

Subsequently, a stereo immersive photography, sometimes referred to as 3D 360 photograph or 3D 360 video, allows an observer to select a perspective of the scene being observed, while each perspective renders into a stereo photograph. A stereo immersive photographic camera generally includes pairs of cameras, thus produces pairs of immersive photographs. The pairs are thereafter stitched to produce an immersive view that contains both sets of visual information, each set intended for each of the observer's eye.

Bracket Positioning During Orthodontic Treatment

One goal of orthodontic treatment is the alignment of the teeth along the dental arch. This can result in a pleasing and aesthetic smile, and well-aligned and coordinated teeth can improve a patient's overall dental health. Achieving this involves aligning all aspects of the teeth: the outer, or labial surfaces of the teeth, the inner, or lingual surfaces, as well as the biting surface, known as the occlusal or incisal surface. Also aligned, although unseen, are the roots of the teeth.

This orthodontic alignment can be accomplished using a combination of orthodontic brackets and archwires to apply biologically compatible forces which cause the teeth to move through bone.

A doctor will bond orthodontic brackets to a patient's malaligned teeth, creating a tooth-bracket unit, such that a force applied to the bracket is transmitted to the tooth. Thereafter, archwires or elastics, or other such orthodontic auxiliaries are used to apply relatively weak orthodontic forces to the brackets for a prolonged time period. The first archwires inserted and attached to the brackets can be extremely flexible, so that they may follow the path through the brackets that are attached to the malaligned teeth.

Archwires can have a component of shape memory. That is, from the initial smooth curved shape of the wire, once attached to the malaligned tooth bracket unit, the wire is deformed. As the archwire tends to return to its original smooth curved shape, it moves the tooth bracket unit closer into alignment. As the tooth alignment improves, stronger and less flexible archwires are incrementally utilized in order to place the teeth increasingly closer to their final alignment.

The archwires may exert forces to a tooth in various directions, namely up-down, in-out, tip, torque and rotation. Achieving accuracy through this process can be technically challenging.

This process continues, until the teeth have become aligned along the target arch form and the malocclusion has been treated. A dental arch form is the arch, formed by the buccal and facial surfaces of the teeth when viewed from their occlusal surfaces.

Since the archwire has the shape of the arch that the treatment aims to achieve, in theory the brackets can be glued once at the beginning of the treatment and remain in place throughout treatment while only the archwires are changed.

To attach the bracket, orthodontic health practitioners glue the brackets at the correct location on each tooth at the beginning of treatment, when the teeth are not yet aligned, so that at the end of treatment, when the teeth become aligned, a perfect archwire exerts no more force and sits in place passively, all the teeth having been aligned in the dental arch.

Accurately bonding orthodontic brackets with repeatable and predictable success is a difficult task even for experienced orthodontists. An orthodontist grasps a placement tool for manually placing a bracket on a tooth, a process that inherently introduces inaccuracies to the achieved result. For example, an orthodontist may attempt to position a bracket at a certain number of millimeters from the edge of the tooth, and due to inherent tolerances in the manual positioning process, the result achieved is half a millimeter off. Thus, occasionally, a bracket has to be removed and repositioned during treatment due to operator error or variation of tooth anatomy in order to accomplish correct tooth alignment.

In an attempt to improve the success rate of initial bracket placement, in recent years expert services were introduced, providing orthodontists with placement aids customized for the patient. One such aid is the use of a "jig" attached to the bracket. The jig is designed for a particular tooth of a particular patient, and it allows the orthodontist to glue the bracket in a precise location.

One method of producing such a personalized jig is by using a computer aided process, which allows an expert to simulate the end arch form of the particular patient's teeth. Simulating an archwire placed on the simulated end arch form assists a doctor or dental technician to precisely locate the correct placement of the bracket on each of the patient's simulated teeth. The simulated archwire sits passively, without exerting forces, in all the simulated brackets when the simulated teeth are aligned. Since brackets are expected, at least in theory, to remain in the same position on the tooth throughout treatment, the same exact bracket location is used as the initial bracket position. A jig is produced to transfer this bracket position to the malaligned tooth.

In some techniques the doctor acquires a 3D model of the patient's teeth, being either a plaster model or an intra-oral digital impression (3D scan), and sends it to a professional service for design of the treatment, a process known as a "set up", that includes the fabrication of the jigs which will be used to accurately place the brackets on the patient's teeth. Frequently, the 3D models or scans are imperfect. In such cases additional information, for example, photos of the patient's mouth, are used to evaluate and fix their deficiencies.

Such automation process may result in highly accurate jigs, perhaps to the order of a tenth of a millimeter error, or even less, thus if a jig is positioned correctly on a tooth, and a bracket is accurately attached with respect to the jig, a high placement accuracy may be achieved. Nonetheless, positioning the jig itself on a tooth, being a manual procedure, is also prone to errors and is difficult to ensure accuracy with a high degree of certainty. To alleviate this problem brackets that have been arranged by a professional service can be initially bonded to mal-positioned teeth in groupings, affording a more accurate jig placement than individual bracket-jig units. The more teeth included in a jig grouping the more contact areas there are to help precisely place the jig and reduce the likelihood of improper bracket placement.

Unfortunately, the bonding that attaches the brackets to the teeth can fail for any number of reasons, one of them being excessive force from biting down on hard foods or objects. This can negatively impact a patient's treatment, causing extended treatment times, reduced treatment efficiency, poor tooth alignment, or a combination of any of the above. Replacing a customized bracket precisely in its original position on a tooth can be challenging. Often times the original jig, if adapted to more than one tooth, will no longer be useful, as the adjacent teeth now have a different relationship as compared to the original pre-treatment malocclusion. The doctor must estimate the correct position to replace the failed bracket, or use a single unit placement jig. This affords a less predictable bonding location due to the inherent instability of a single unit jig placed on a single tooth, as there are fewer contact points to provide stability to the jig. For this reason, jigs are helpful during the initial placement, but are mostly unhelpful for the replacement of brackets that detach during the prolonged treatment.

Stock, or "off the shelf" brackets are designed to give an average position to the tooth, depending on the clinical preferences of the doctor. Stock brackets were not customized to a particular patient, and are substantially less costly. Jigs may be created for such brackets but the cost of customized jigs may negate the lower cost offered by the standard workflow.

Placement of such brackets requires an in-depth understanding of dental anatomy and occlusion, as well as an appreciation of the art and science of orthodontic treatment. A similar challenge faced by a doctor is when a dental auxiliary is tasked with initial bracket placement, even when an accompanying jig is available. In order to achieve accurate placement while using a jig, the jig itself must be attached correctly to the teeth. But the surface of some teeth, for example the incisors, do not have a distinctive enough anatomy necessary to lock the plastic made jig into a predefine position, enabling to mislocate the jig introducing large errors to the bracket placement, a small error in attaching the jig to the occlusal edge of the teeth translates to an error of the angle the jig has with respect to the teeth, and may result in a large error, of a magnitude of half a millimeter or even more, in the placement of the brackets. Other problems may arise due to the shift in position of a patient's teeth, especially the molars of younger patients, during the few weeks period between the time a dental impression is generated and the time of the following patient visit where bonding of orthodontic appliances occurs. This causes the jig to become inaccurate since it does not reflect the current surfaces of the teeth. Thus an orthodontic may have to assess the resulting placement and oftentimes will need to debond and reposition inaccurately placed brackets, thereby extending treatment time and reducing practice efficiency.

In the event that an orthodontic bracket has been bonded on a tooth in an inaccurate position, orthodontic treatment results may be compromised. In this situation the doctor may elect to remove the bracket and replace the same bracket, or a new bracket, in a more ideal position to achieve the desired tooth position. Many doctors refer to this as "repositioning". An area of frustration is when the doctor repositions the bracket and then realizes that the newly repositioned bracket remains in a less than ideal position.

Methods and systems are needed to position orthodontic brackets throughout the prolonged treatment more accurately and efficiently.

BRIEF SUMMARY

In an embodiment, an input indicating a location selected by a health care professional on an image showing a perspective of an immersive photographic model of a patient's mouth to indicate a position to place an orthodontic bracket on a patient's tooth is received. An immersive photographic model allows selecting a center point as well as an angle around the center point when choosing a perspective, providing a sense of depth. A ray is extended from a focal point of a viewport, representing the desired perspective, at a direction determined based on the input. An intersection of two or more rays in a three-dimensional space is determined. The intersection indicates a position to place the orthodontic bracket on the patient's tooth.

System, device, and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

The drawing in which an element first appears is typically indicated by the leftmost digit or digits in the corresponding reference number. In the drawings, like reference numbers may indicate identical or functionally similar elements.

DETAILED DESCRIPTION

The present specification discloses an apparatus, system and method for determining and marking the proper placement of orthodontic brackets. In particular, an orthodontist selects placement for a simulated bracket on an image rendered with respect to a viewport mapped onto an immersive photographic model of a patient's mouth. Subsequently, another health care practitioner may observe the immersive view superimposed with simulated brackets as guidance for correctly placing actual brackets in the patient's mouth, at the determined locations.

The following detailed description is divided in four sections. First, the description explains how the placement of orthodontic brackets can be determined using immersive photographs with respect to FIGS. 1A-B and 2A-B. Second, devices that may be used to capture immersive photographs and dental measurements are described with respect to FIGS. 3-7. Third, systems and methods are described that guide placement of orthodontic brackets with respect to FIGS. 8-10 and 11A-B. Fourth and finally, systems and methods that generate immersive photographic models and digital dental impressions from imagery data are described with respect to FIGS. 12 and 13A-B.

I. DETERMINING PLACEMENT OF ORTHODONTIC BRACKETS

Figure 1A:
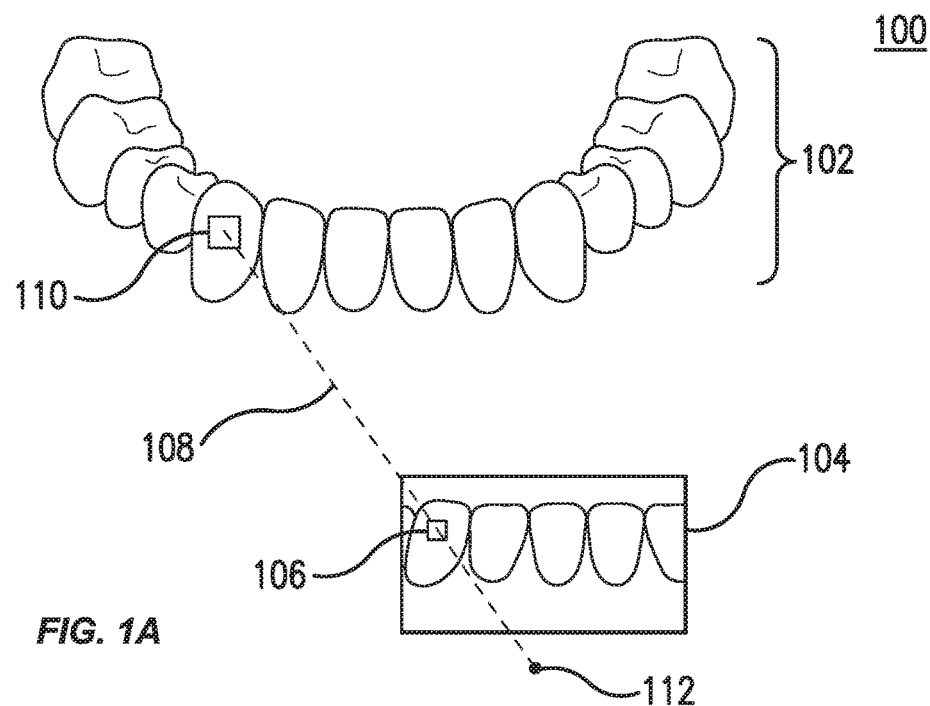
FIGS. 1A-B illustrate using a selection on a viewport for an immersive view photographic image to determine a desired position for an orthodontic bracket.
Figure 1B:
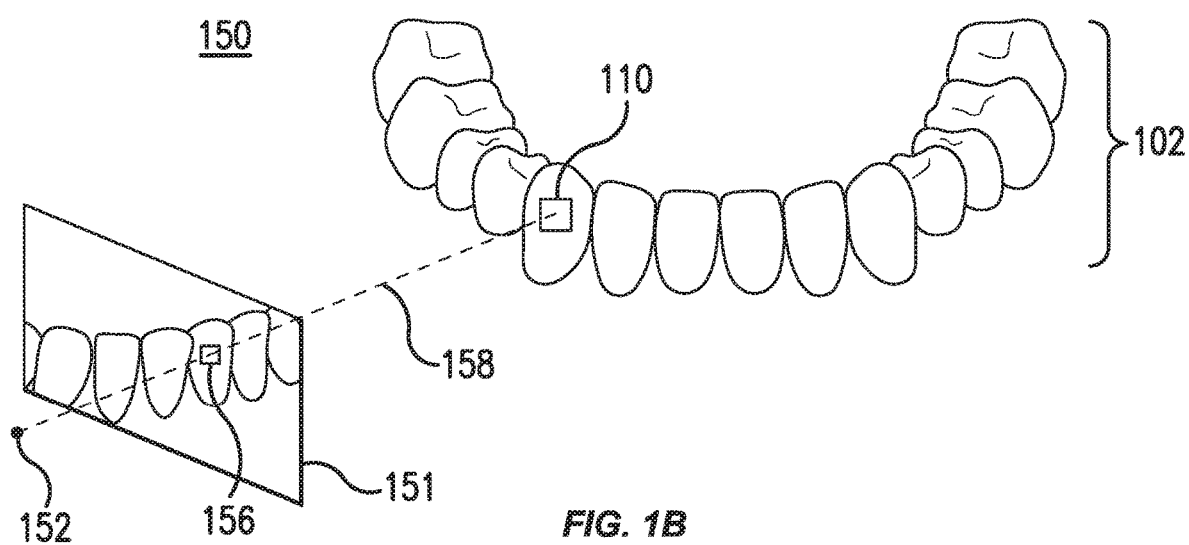

FIGS. 1A-B illustrate using a selection on a viewport for an immersive view photographic image to determine a desired position for an orthodontic bracket. FIG. 1A illustrates a diagram 100 illustrating a visual perception of a patient's mouth 102 and a viewport 104 of an immersive photographic image. Visual perception of a patient's mouth 102 is the way an observer perceives the patient's mouth, including the patient's teeth, while observing an immersive photograph. The reference to an immersive photograph may include both the mono and stereo versions.

The portion of an immersive photographic image illustrated in viewport 104 may have a focal point 112, which may be the position where the immersive photographic image was taken, relative to the patient's teeth as represented by visual perception of a patient's mouth 102. Alternatively, a number of images taken from the area surrounding focal point 112 may be reconstructed so as to appear as if they were taken from a single immersive camera at focal point 112. Viewport 104 may represent the perspective of the immersive photographic image presently displayed. A user, such as an expert orthodontist, may input navigational controls to move viewport 104 to display different perspectives of the immersive photographic image.

Expert orthodontists and technicians may also navigate between immersive photographic images, for example enabling the patient's teeth to be presented from many possible angles with different focal points. As shown, FIG. 1B has a diagram 150 that illustrates another viewport 151 possibly of another immersive photographic image. The immersive photographic image illustrated in viewport 151 was taken at a different location, represented by a focal point 152.

Thus by switching between different viewports, an expert orthodontist can gain understanding of dental surface shape, such as inclinations and dimensions. Since the view is of actual images captured in the patient's mouth, and not a synthetic computer generated model, the experience closely matches that of the expert watching the patient himself. A computerized 3D model of the dental surfaces, such as that generated with a 3D dental scanner, does not need be utilized at all to achieve this visualization purpose, since the human mind seemingly generates the 3D sense. A stereo immersive view will, naturally, increase this perception. In some sense, observing the visual perception of a patient's mouth 102 using this method has an advantage over watching an actual patient visiting the dental office, since practitioners may zoom-in a viewport as close as they desire, an action that may cause discomfort if performed on the patients themselves.

A dental immersive photographic model, or immersive view, can be described as a viewport space together with the respective visual information. In an embodiment, it may be the aggregate of immersive photographs and the locations in 3D space where each of the photographs was taken. In another embodiment it may also include an interpolation between locations in 3D space where photographs was taken to produce a more contiguous viewport space. A viewport would generally render visual information out of multiple images. A video recording input for such a model may result in a virtually continuous viewport space containing the path of the immersive camera in the patient's mouth. When users select a viewport, they select a perspective of the immersive view that includes a location in 3D space out of which they desire to observe and an angle around that location indicating the desired viewing angle.

Returning to FIG. 1A, an expert orthodontist may select location 106 on viewport 104 as the proper location to position an orthodontic bracket to ensure that once attached to an archwire and tensions applied, the teeth will become aligned. Once the expert orthodontist selects location 106 in the photographic image, the perceived location on the patient's teeth corresponding with the location selected in the photographic image must be determined. To determine the perceived location on the patient's teeth, a ray 108 is extended from focal point 112 through the selected location 106 on viewport 104. The distance between focal point 112 and viewport 104 may represent the zoom of the viewport with respect to the immersive photographic image.

In one embodiment, an intersection 110 may be determined as the intersection of ray 108 and another ray extended based on the expert's selection in another viewport of the immersive view. For example, after selecting location 106 on viewport 104, intersection 110 may be determined as someplace along ray 108. Then, the expert may navigate to observe an image through another viewport as illustrated in diagram 150 in FIG. 1B. The other image is rendered into viewport 151. In an embodiment, a visual representation of ray 108 is overlaid onto the other image, and the expert may select a location along the ray's 108 representation. The expert selects a location 156 in viewport 151. Based on the selected location 156, ray 158 is extended from focal point 152 through the selected location 156 on viewport 151. Intersection 110 may be determined as the intersection between rays 108 and 158. The location of intersection 110 in 3D space is calculated with reference to locations defined by the immersive photography model, for example, the same reference by which locations of focal point 112 and 152 are defined. In this way, intersection 110 may be determined without the need for a digital dental impression data, which represents the surface of the patient's teeth, at all.

An expert may select a bracket from a bracket library to be used on the patient. Brackets differ in dimensions and purpose. For example, some brackets are marketed as part of an orthodontic "system", whereby different teeth are assigned differently shaped brackets in order to allow the dentist to use a simple curved archwire to obtain the desired clinical result. These brackets are designed to take into account the anatomy and shape of different teeth, or designed to achieve a different desired orthodontic goal, and are intended to be placed in some standardized position as determined by the manufacturer. These "systems" each have unique characteristics and as such the expert chooses the system selected by the doctor.

A 3D model of the bracket from the library is then superimposed onto the viewport space of the immersive photographic model. To superimpose the position of the bracket, a computer program can render an image of the 3D bracket model from the perspective of focal point 112. One option is for the computer program to set the bracket initial position in 3D space at intersection 110. Then, the program can overlay the rendered bracket onto the image presented through viewport 104. If required, an expert can now manipulate the position and size of the simulated bracket until it seems that it is properly located on a tooth, that is from various viewports a rendered image that includes a perspective of visual perception of a patient's mouth 102 superimposed with the simulated bracket looks as if the bracket is correctly attached to the tooth. While this is only an illusion, since 3D information of the tooth is not necessarily available, it provides a substantially realistic sense due to the realistic interpretation given to the rendered images by the human mind. Therefore it will become a useful tool to communicate to another health care provider the desired position of the bracket when actually placed in the patient's mouth.

The bracket may presently be viewed from various angles. Turning to FIG. 1B, the bracket may be rendered from the perspective of focal point 152. The rendered bracket may presently appear on the image rendered to viewport 154 at position 156.

The gluing or bonding of a bracket to a tooth adds some spacer between the tooth and the bracket. This spacer is sometimes used to add more torque exerted by the bracket. This spacer may also be simulated in the rendering for improved accuracy.

In some scenarios, a full 3D simulation of a bracket is not necessary, and it is sufficient for the expert to superimpose a mark, for example a thin rectangle, onto the viewport space that will be rendered on a tooth designating the desired bracket placement.

Generally, an expert may have to choose the dimension of the bracket, scaling it to fit the perceived dimensions of the tooth as visualized. But if using a 3D scan of the tooth, or alternatively at least one of the 2D images being rendered includes measurements of the tooth of interest, the simulated bracket can be automatically scaled to fit the dimensions. Such dental measurements, for example, may be made by a health care provider using a measurement tool such as a periodontal probe or caliper. Health care providers may input their dental measurements to a computer program system. Additionally, a health care provider may use a periodontal probe or caliper to perform a measurement while images are being captured, there after a computer program may extract the measurement readings by analyzing the images. Another method to add measurements is by using the properties of image overlapping and object scale. We will see below that embodiments include several image sensors and that neighboring or nearby image sensors may capture images that have overlapping portions. Due to geometric considerations, the closer the cameras are to an object being captured, the overlapping sections becomes smaller. Using this property, a computer program may estimate the dimensions of the object, and perhaps its distance from the camera. Another technique to estimate the dimensions of an object is by using images of the object captured from two or more angles. Just as the intersections of rays 108 and 158, as described for FIG. 1A-1B, enabled a computer program to determine a point in space corresponding to the location of a tooth, two intersections, each of a pair of rays, the two pairs of rays extended towards opposing edges of an object may determine two points on opposing edges of an object allowing to calculate a dimension of the object as the distance between the points. The points towards which the rays are extended may be selected by an operator or by a computer program. In some embodiments, the ability to extract measurements may be used to generate a dental impression of at least part of a patient's mouth, as discussed below.

Using the selection of bracket placement on an immersive view, embodiments guide orthodontists during the actual bracket placement. In addition, embodiments allow placement decisions to occur in a back office process, either by the same health care provider that will be actually placing the brackets, or by someone else, for example by an expert orthodontist. By placing placement decisions in a back-office process, and providing guidance during the bracket installation process, the health care practitioner installing the brackets may be more effective in placing the bracket exactly at the desired location when the patient arrives for treatment, even in the cases where the practitioner is not an expert in this art.

Just as a simulated 3D bracket may be superimposed onto the viewport space, additional synthetic 3D models of objects may be superimposed. One of the possibilities is to superimpose a 3D dental impression of the patient's mouth. Once superimposed, a user may adjust the location and the scale of the synthetic impression within the viewport space, so that the result matches the location and scale of the visual perception of the patient's mouth 102 as generated by the immersive view and shown in FIG. 1A-1B. One method to adjust the location and the scale of the impression is by selecting three or more points on a rendering of the impression, and also selecting matching points through viewports of the immersive view, each of the latter points selected as described in relation to FIG. 1A-1B. After selecting matching points, a computer program may adjust the location and scale of the impression 3D mesh within the viewport space. The mesh representing the impression may now be defined within the space, even if it is not being rendered for viewing. Back to FIG. 1A-1B, it would suggest that the impression is located where visual perception 102 is. An advantage to performing such a procedure is that now a ray 108 extended from focal point 112 through the selected location 106 may intersect with the impression mesh at intersection 110. Thus intersection 110 may be determined with a single selection.

Figure 2A:
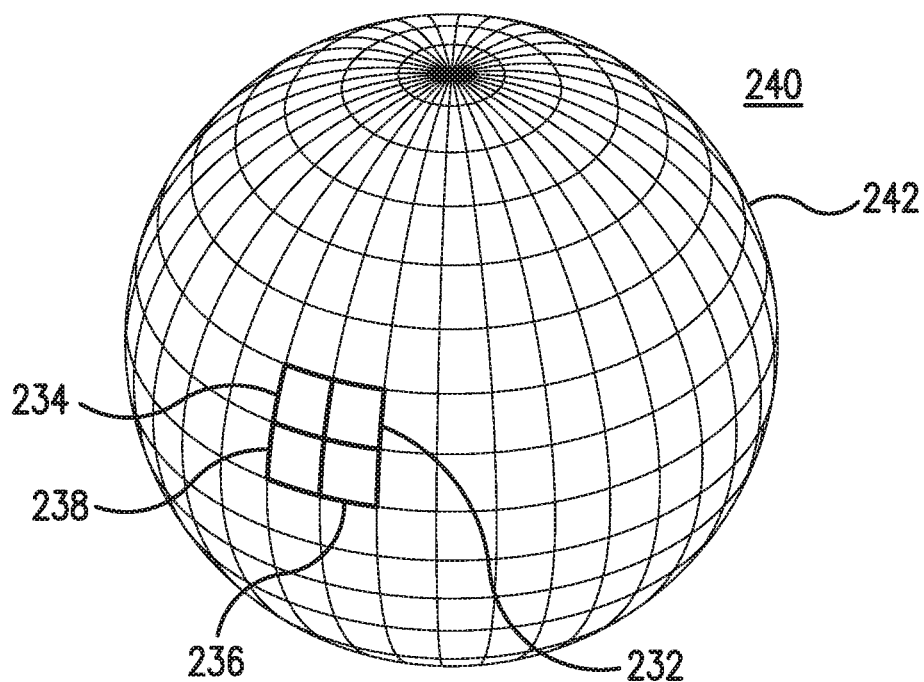
FIGS. 2A-B are diagrams illustrating an immersive photographic image and rendering it to a viewport.
Figure 2B:
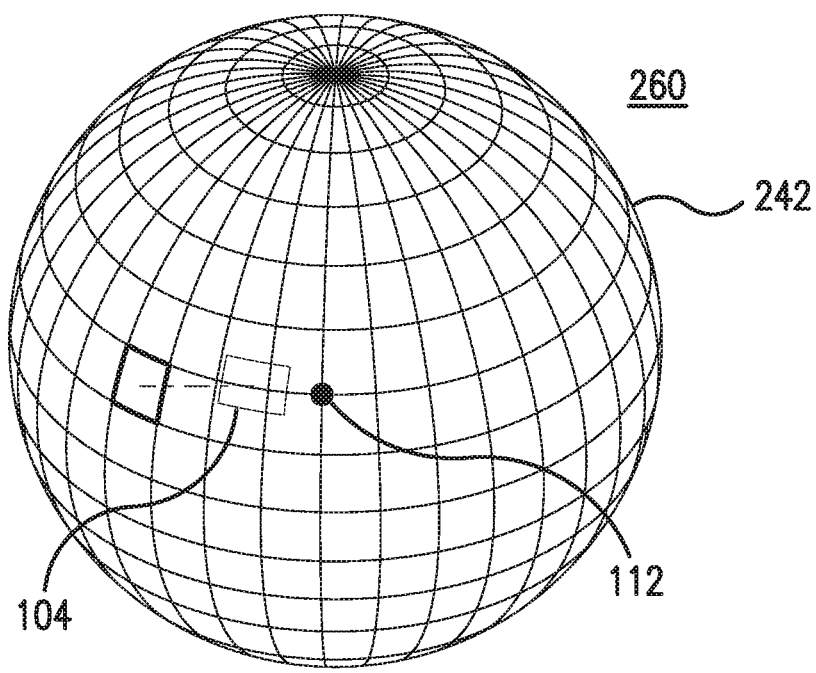

FIGS. 2A-B are diagrams illustrating an immersive photographic image and rendering it to a viewport. As is discussed in more detail below, an immersive photographic image may be generated from multiple image sensors oriented in different directions so as to capture multiple photographs from different perspectives simultaneously.

Alternatively, an immersive photograph image may be generated by a single image sensor that is rotated to capture photographs from different directions. For example, the motion of the immersive camera in the intraoral environment while recording immersive photographs renders a multitude of such photographs.

Based on associated position information for the respective photographs and perhaps correlating features between photographs, photographic images captured from the image sensors are mapped into a sphere. The photographs are each mapped according to the angle from which it was captured relative to the center of the sphere which represents the capturing location, as shown in FIG. 2A.

FIG. 2A shows a diagram 240 with a sphere 242 with pixels from images 232, 234, 236, and 238 mapped to it. Diagram 240 shows the alignment of images along the surface of a sphere. A sphere is an appropriate shape for aligning the images from a device with embedded cameras positioned along a spherical shape. If the combined field of view of all the embedded cameras having respective overlapping areas covers a sphere, then the images can be aligned to cover a complete sphere. Otherwise, some areas of the sphere may not have visuals information. In some embodiments, where a handle is attached to a spherical shape with such embedded cameras, the areas around the handle may not include cameras. Possibly this area is of lesser interest for recording.

The sphere 242 represents one immersive photograph. Multiple such spheres (not shown) may be created, for example through the recording of video, with center points in various locations inside the patient's mouth. The aggregation of such spheres maps a viewport space. Later on, while observing the immersive photographs, a health care provider may choose a viewport from of the viewport space, and hence a position within the mouth and an angle around that position, defining the perspective he is interested in viewing as described in FIGS. 1A and 1B.

Using the sphere 242, an image can be rendered to the user in a way that provides a sense of depth, as illustrated in FIG. 2B.

FIG. 2B shows a diagram 260 illustrating the geometry for rendering a viewport out of such an immersive photograph. The selection of a desired perspective-a focal point in space and a viewing angle around that point—is sometimes referred to as selecting a position of a virtual camera, the camera supposedly captures the perspective of the scene for presentation. In diagram 260, the immersive photograph is rendered according to a virtual camera corresponding to viewport 104 and focal point 112 as illustrated in FIG. 1A. Viewpoint 104 may be specified by a point in space-focal point 112, here at the center of the sphere—and a field of view emanating from this point. A health care provider chooses an angle for the virtual camera and accordingly viewport 104 is determined. The pixels of the sphere are mapped into viewport 104 to produce an image for display. A health care provider may then choose to "rotate" the camera around the center point, rotating the viewport as well for displaying various angles of the mouth around the same center point. When the virtual camera changes perspective, a different sphere is selected or a different portion of the sphere is mapped to viewport 104, resulting in rendering a different subject matter from the immersive photography model.

In the depicted embodiment, viewport 104 is located within the sphere. Given a viewport, a computer program can render for presentation a corresponding image out of the sphere of aligned images, for example, by tracing rays from the sphere's center point, through the viewport and to the sphere's surface. Naturally, this mapping may be processed separately from the visualization to allow a faster response to an observer's requests. For an observer manipulating the viewport, shifting a viewport radially outwards is equivalent to zooming in on the presented image.

In this way, an orthodontics expert can navigate within photographic images of the patient's mouth.

II. DEVICES FOR CAPTURING IMMERSIVE PHOTOGRAPHIC IMAGES AND 3-D DENTAL IMPRESSIONS

Devices that may be used to capture immersive photographs and digital dental impressions are described with respect to FIGS. 3-7.

Figure 3:
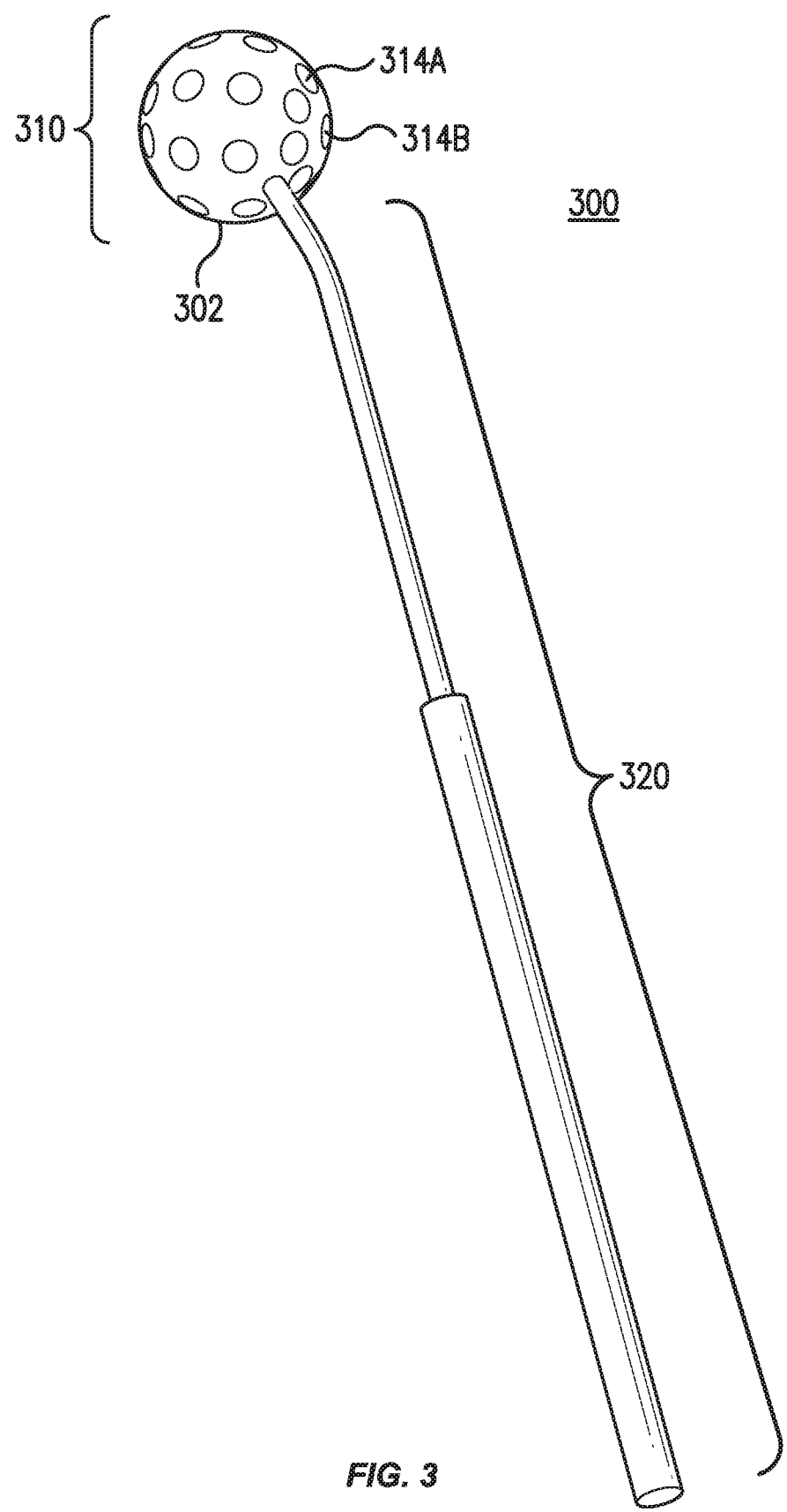
FIG. 3 is a diagram illustrating an intraoral immersive photographic camera.

FIG. 3 is a diagram illustrating an intraoral immersive photographic camera 300. Intraoral immersive photographic camera 300 includes a camera head 310 and a handle 320 that enables a health care provider to grasp the dental instrument. The camera head 310, which in the depicted embodiment has the shape of a sphere 302 includes a protective shell that physically separates the electronics inside the camera head 310 from the intraoral environment. The sphere 302 includes pass-through surfaces, for example 314A and 314B, that allow the integrated cameras (not shown) to capture images of the intraoral environment. Some of the pass-through surfaces may allow light emitted by the immersive photography camera illuminating devices (not shown) to illuminate the intraoral environment. A pass-through surface may simply be an opening. It may also be, for example, a one-way mirror, configured such that light is able to pass-through it in the desired direction.

An image captured by one embedded camera overlaps images captured by one or more of the neighboring or nearby cameras. This affects the geometric arrangements of the cameras. For example, a camera may have a 90 degrees field of view. In the short distances that exist between a camera and an object within an intraoral environment, the visual information captured above 70 degrees of field of view may suffer irreparable distortion, usually of the form of the so-called barrel distortion. Such distortion may impede the image to become aligned to an adjacent image. Thus, to allow 10 degrees of overlapping for alignment, the cameras should be arranged in such a way that the angle between the center of the field of view of any two adjacent cameras is no more than 60 degrees.

Figure 4A:
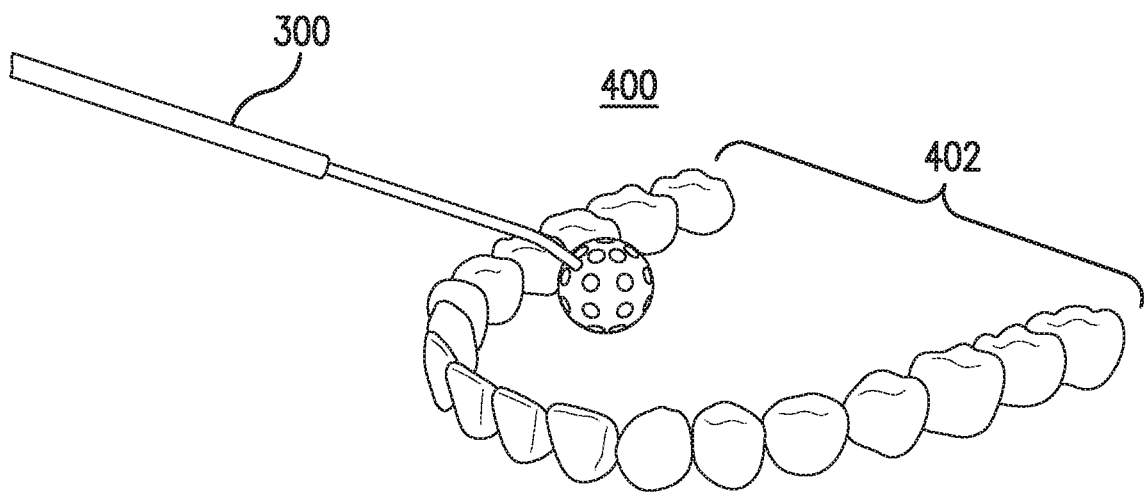
FIGS. 4A-B are diagrams illustrating capture of an immersive photograph at an intra-oral location.
Figure 4B:
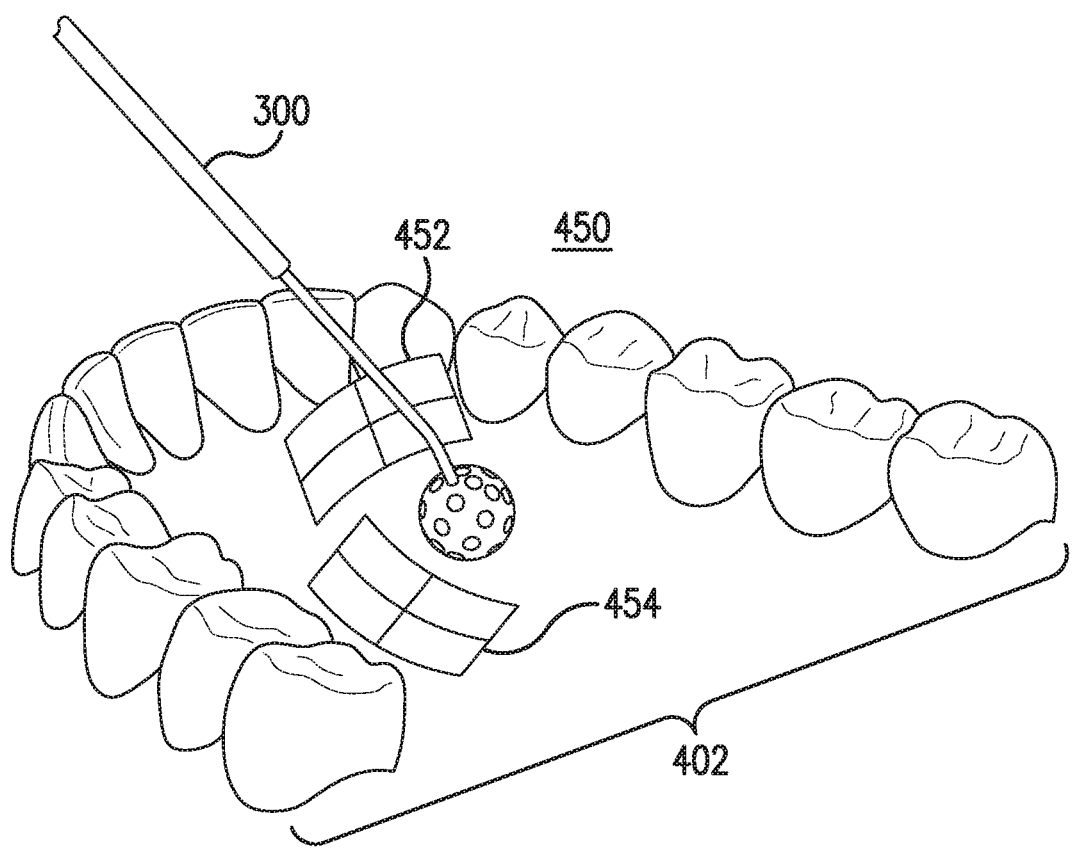

FIGS. 4A-B are diagrams illustrating capture of an immersive photograph at an intra-oral location. FIG. 4A shows a diagram 400 illustrating intraoral immersive photographic camera 300 in an intraoral environment 402. While intraoral immersive photographic camera 300 is moving around intraoral environment 402, it is capturing an immersive video. The image sensors capture images and video, while the accelerator and gyroscope capture a position and rotation of the camera.

FIG. 4B illustrates a diagram 450 showing images captured by immersive photographic camera 300 inside the patient's mouth. In particular, diagram 450 shows intraoral environment 402 and depicts how a camera takes images from the same location but at different angles. The images captured from different image sensors on immersive photographic camera 300 are shown as photographic images 452 and 454 of the interior of a patient's mouth. Images 452 and 454 are each captured from an image sensor affixed to camera 300. The images 452 and 454 are captured nearly simultaneously, before the immersive photographic camera has substantially moved to another location.

Figure 5:
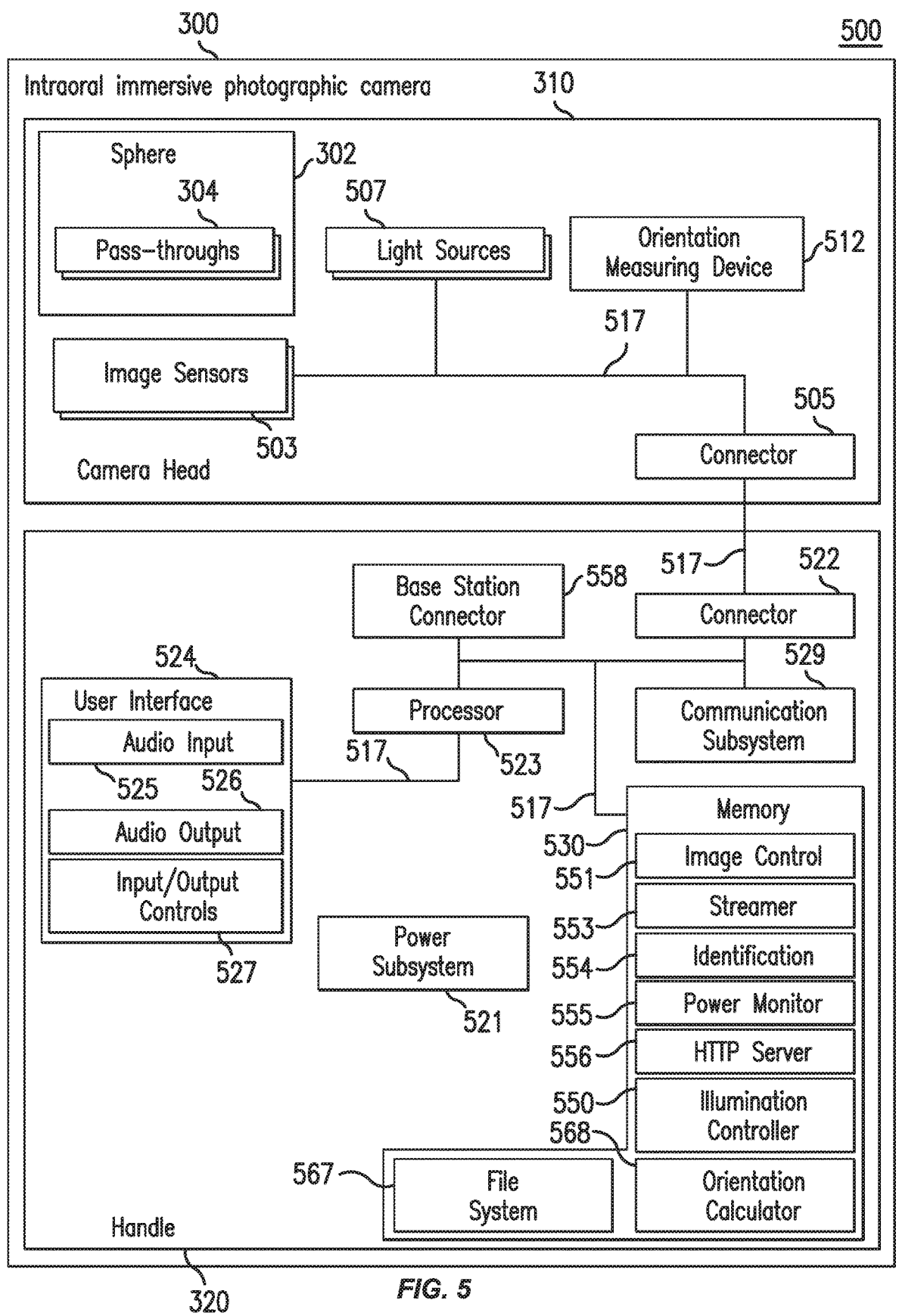
FIG. 5 is a system diagram of the intraoral immersive photographic camera.

FIG. 5 is a system diagram 500 illustrating a possible configuration of intraoral immersive photographic camera 300. As discussed above, camera 300 has two components, camera head 310 and handle 320, and camera head 310 includes sphere 302, image sensor(s) 503, light source(s) 507, an orientation measuring device 512, and a connector 505. In an embodiment, camera head 310 may be the portion that is inserted into the patient's mouth and is autoclavable, while handle 320 may not be autoclavable.

It may be appreciated for those skilled in the art that a plurality of signal lines or buses 517 may exist, thus different components may be linked by different signal lines or buses 517, and that signal lines or buses 517 depicted in the schematic diagram may represent a plurality of such.

Sphere 302 includes a plurality of pass-throughs 304. A pass-through 304 allows the pass-through of light or visual information to allow light or visual information to reach image sensor 503 (so that a respective image can be captured) or to allow illumination of objects by light from light source 507. In some embodiments, pass-through 304 is an opening in sphere 302. In some embodiments, pass-through 304 is a transparent, semi-transparent, or partially-transparent area in sphere 302. In some embodiments, pass-through 304 includes an optical lens. In some embodiments, pass-through 304 is a section of the area of sphere 302 that becomes transparent or partially transparent when light, possibly of an intensity above some threshold, is present. In some embodiments, pass-through 304 is a section of the area of sphere 302 that becomes transparent or partially transparent when electrical current or voltage is present. In some embodiments, pass-through 304 provides physical separation from the environment to other of camera head 310's components, for example image sensor 503, when camera head 310 is operating in an intraoral environment, or during sterilization or the like.

As described above, pass-throughs 304 may transmit light to/from an image sensor 503 or a light source 507. Image sensor 503 captures still or video digital images. In some embodiments, image sensor 503 is an image sensor, or plurality thereof, that includes a pixel array, such as a charged coupled device (CCD), or a complementary metal-oxide-semiconductor (CMOS) sensor, or the like. An example of an image sensor is the MT9V023 available from ON Semiconductor of Phoenix, Ariz. In some embodiments, image sensor 503 is part of a system-on-chip (SOC) with image sensing capabilities. The SOC may include a memory and/or an image signal processor (ISP) or other components. An example for such an SOC is the OV5640 available from OmniVision Technologies Inc. of Santa Clara, Calif. In some embodiments, image sensor 503 includes one or more optical lenses.

Light source 507 illuminates objects in the proximity of camera 300. In some embodiments, light source 507 illuminates areas of a person's mouth to improve the image captured by image sensor 503. In some embodiments, a plurality of light sources 507 are included. In some embodiments, light source 507 emits light. In some embodiments, light source 507 transmits light emitted elsewhere in camera 300. In some embodiments, the intensity of the light emitted or transmitted by light source 507 can be controlled. In some embodiments, the intensity of illumination by a plurality of light sources 507 is concurrently controlled. In some embodiments, the intensity of each light source 507 of a plurality of light sources 507 is independently controlled. In some embodiments, a plurality of light sources 507 all emit or transmit the same or similar light wavelengths (or colors). In some embodiments, different wavelengths (or colors) may be emitted or transmitted by a plurality of light sources 507. In some embodiments, light source 507 is a led emitting diode (LED). In some embodiments, light source 507 is a light pipe, such as an optical fiber cable or the like. It can be appreciated that other devices can be used as light source 507 to illuminate areas of a mouth without departing from the spirit of the present invention. In some embodiments, light source 507 is a monochromatic light (a laser). In some embodiments, light source 507 transmits light emitted by a laser. In some embodiments, light sources 507 are located close to the internal surface of sphere 302. In some embodiments, light source 507 may be located at a different location of sphere 302 and/or elsewhere in camera head 310. In some embodiments, the light emitted and/or transmitted by light source 507 passes through a pass-through 304. In some embodiments, light source 507 is physically separated from the environment (for example an intraoral environment or sterilization environment) by a pass-through 304. In some embodiment, light sources 507 or pass-through 304 are evenly distributed across the surface of sphere 302.

Orientation measuring device 512 measures an orientation (including x,y,z, position and yaw, pitch, roll direction) of sphere 302 or generates data that enables to calculate an orientation of sphere 302. In some embodiments, orientation measuring device 512 is an accelerometer. An example of an accelerometer is MMA8453Q available from NXP Semiconductors N.V. of Eindhoven, Netherlands. In some embodiments, orientation measuring device 512 is a gyroscope. An example of a gyroscope is FXAS21002C also available from NXP Semiconductors N.V.

Turning to handle 320, handle 320 includes a user interface 524, a processor 523, a base station connector 558, a connector 522, a communication subsystem 529, a power subsystem 521, and a memory 530.

Base station connector 558 enables handle 320 which may or may not be attached to a camera head 310 to dock with a base station. The docking may occur through a physical connection which holds handle 320 at a predefined orientation. In addition, the docking may occur through a USB or near field communication connection or the like. When docking with the base station, handle 320 may receive electrical power through base station connector 558, which may be used to charge power subsystem 521. In addition, handle 320 may receive control and signaling information through base station connector 558. For example, base station connector 558 may receive information needed to configure a wireless communication connection between handle 320 and the base station. Base station connector 558 may provide the wireless configuration information (such as a service set identifier and password) to communication subsystem 529, as is discussed below. And, when docked to a base station, base station connector 558 may signal orientation measuring device 512 or software in memory 530 to calibrate. In addition, when handle 320 is docked to a base station, the base station may receive some or all of the collected data that is stored, as discussed below, in memory 530.

Power subsystem 521 stores power for camera 300 and provides power to the other components of camera 300. Power subsystem 521 may include batteries, such as AAAA batteries, or a capacitor.

User interface 524 includes an audio input 525, audio output 526, and input/output controls 527. Audio input 525 captures audial information. In some embodiments, audio input 525 includes a microphone. In some embodiments, audio input 525 captures human voice, for example, to enable a healthcare provider to dictate observations for a patient's medical record. Handle 320 includes an audio output 526, which emits sounds. In some embodiments, audio output 526 includes one or more speakers. In some embodiments, audio output 526 includes headphone jacks and/or headphones.

Input/output controls 527 can include buttons, lights, knobs, capacitive sensors, actuators for haptic feedback or the like for a user to control and/or receive feedback relating to processes in camera 300, for example, to initiate audio recording or image capturing, or set an intensity of illumination.

Communication subsystem 529 allows handle 320 to connect to one or more remote computational devices, including, for example, to a base station, or to a general purpose computational device such as personal computer, a smart phone, a tablet or similar, or a specialized computational device such as to another intraoral immersive photographic camera or remote speakers or the like. In some embodiments, communication subsystem 529 is adapted to connect to a wireless network, including, but not limited to, WiFi and/or Bluetooth. In some embodiments, communication subsystem 529 is adapted to attach to a wired network, including, but not limited to, Ethernet, USB or thunderbolt.

Memory 530 may include random access memory (RAM) and may also include nonvolatile memory, such as read only memory (ROM) and/or flash memory. Memory 530 may be an independent memory component, or may be embedded in another component, such as processor 523 and/or image sensor 503, or may be a combination of two, or may include a plurality of memory components. Memory 530 may include a detachable memory module such as a flash memory card. Memory 530 is adapted to include software modules (a module is a set of instructions). In particular, memory 530 includes a streamer module 553, identification module 554, power monitor module 555, HTTP server module 556, illumination controller module 550, image control module 551, file system module 567 and orientation calculator module 568.

Processor 523 is adapted to run instructions stored in memory 530. Processor 523 may be a micro-controller unit (MCU), a digital signal processor (DSP) and/or an Image/Video Processing unit or like components that run instructions. An example of an MCU is MSP432P401x available from Texas Instruments Inc. of Dallas, Tex. An example of a DSP is C5000 available from Texas Instruments Inc. of Dallas, Tex. An example of an image/video processor is OMAP3525 available from Texas Instruments Inc. of Dallas, Tex. One or more processors 523 may be present. Processor 523 may be an independent component, it may also be embedded in another component, such as in image sensor 503, or any combination thereof.

In some configurations, head 310 and handle 320 are separable components. In those cases, connector 505 of camera head 310 connects (physically and/or electronically) to connector 522 of handle 320, bridging the respective sections of bus 517. Image sensor 503 and light source 507 receive electrical power from handle 320 through connector

505. In addition, control and signaling is passed to and from image sensor 503 and light source 507 through connector 505. For example, image sensor 503 may transmit images captured via bus 517 to connector 505, which transmits images to handle 320. Similarly, connector 505 may receive and pass along control information indicating when and whether to activate image sensor 503. For light source 507, connector 505 may receive commands on which light sources 507 to activate and when and how to activate them. Connector 505 is adapted to connect to a connector 522 in handle 320. In some embodiments, connector 505 and connector 522 may include a light connector, allowing transmission of light between handle 320 and camera head 310.

Illumination controller module 550 controls the operation of light source 507. In some embodiments, illumination controller module 550 sets the intensity of illumination of light source 507. In some embodiments, illumination controller module 550 receives a user request to increase or reduce illumination. In some embodiments, illumination controller module 550 receives a user request to turn on or off some or all of light source 507. In some embodiments, illumination controller module 550 receives requests from other software modules to increase and/or decrease illumination of one or more of light source 507. In some embodiments, user input as well as said requests are used to determine an intensity of illumination.

Orientation calculator module 568 reads data from orientation measuring device 512. Orientation calculator module 568 may, for example, integrate data from a gyroscope and accelerometer to determine a location (in, for example, x,y,z coordinates) and a direction (for example, yaw, pitch, and roll). Because orientation calculator module 568 uses integration to determine the location and direction of camera 300, errors from the gyroscope and the accelerometer can accumulate over time. However, as described above, base station connector 558 may dock with the base station in such a way to position handle 320 at a known angle. When base station connector 558 is docked with the base station, base station connector 558 may signal orientation calculator module 568 to calibrate. To calibrate, orientation calculator module 568 may set the x, y, z, and yaw, pitch, and roll values to fixed values, such as the value zero, or may retrieve, for storing in memory 530 or for transmitting these values to the base station, to be used as offsets to its location when it is no longer docked. Thus, when handle 320 is moved around, the coordinate and direction values orientation calculator module 568 determines may be relative to the coordinate and direction values set at the base station.

Image control module 551 controls the capture of images and video, and thus may affect the output image quality. In some embodiments, image control module 551 controls the intensity of illumination, for example, by requests to illumination controller module 550, for example to improve the illumination conditions for a better image capture quality. In some embodiments, image control module 551 processes a set of time-successive images to create a single output image which has an improved visual quality, for example, but not limited to by selecting one image out of the set, or by combining portions of images, each portion from an image in the set. In some embodiments, values indicating the acceleration of image sensor 503 when an image was captured are used to improve the quality of an output image, for example, but not limited to, selecting images with least acceleration or interpolating among portions of two or more images of different acceleration. In some embodiments, image control module 551 controls the aperture and/or focal point of a lens. In some embodiments, image control module 551 triggers the capture of a sequence of images each with a different illumination. In some embodiments, image control module 551 triggers the capture of a sequence of images each with a possibly different group of one or more of light sources 507 set to illuminate, while the other one or more of light source 507 set to not illuminate. In some embodiments, image control module 551 may assemble multiple images from multiple image sensors into a single immersive view.

Identification module 554 identifies camera 300 to a remote computational device. In some embodiments, identification module 554 implements an authentication handshake protocol in which the identification occurs over a network session. In some embodiments, identification module 554 couples an identification to data prior to the data being transferred to a remote computational device. The identification may include a globally unique ID for handle 320. It may also be timestamped and digitally signed.

Power monitor module 555 monitors the amount of energy available by the power subsystem, and the power usage of camera 300. In some embodiments, power monitor module 555 receives a motion indication generated by orientation measuring device 512, for example, but not limited to, an acceleration indication. In some embodiments, power monitor module 555 sets camera 300 into a standby mode when camera 300 is not being used for a time interval larger than some threshold. To set a standby mode, in which camera 300 consumes a reduced amount of power, power monitor module 555 may reduce or completely shut down the power supply to some of camera 300's components and/or alter or completely pause some of camera 300's software processes, or the like. In some embodiments, power monitor module 555 exits a standby mode, for example, by resuming power to some of camera 300's components or resuming execution of some of camera 300's processes, when an indication of usage of camera 300 is present. In some embodiments, power monitor module 555 enters or exits a standby mode based on other parameters or indications, however the invention is not so limited. In some embodiments, power monitor 555 performs a shutdown, shutting power to more (when compared to standby mode) or even all of camera 300 components, when an indication of not being used is present for a time interval larger than some threshold, or based on other parameters or indications.

Streamer module 553 prepares and/or streams data to another computational device through communication system 529. The data can include video collected from image sensor 503, location information including camera 300's orientation and location collected from orientation calculator module 568, audio input collected from audio input 525, any data collected from input/output controls 527, power-related data, such as power remaining or rate of power consumption, collected from power monitor 555 and the specification of how light source 507 is illuminated from illumination controller module 550. Streamer module 553 may associate data collected from these various sources with each other. To associate data collected from different sources, streamer module 553 may attach a timestamp. For example, each frame in video image sensor 503 may include a timestamp which is collected. Similarly, the orientation, audio, power, and input control information may have a timestamp indicating when that information was collected, and the illumination information may have a timestamp indicating when light source 507 was illuminated in the manner specified. Streamer module 553 may store some or all of the collected data to memory 530. This may be useful, for example, in embodiments, where limitations to the available data transmission bandwidth may impede streaming data immediately following its collection. The stored data may then be transmitted at a later time. For example, in some embodiments, the video collected from the images sensor is stored in memory 530, while other collected data, for example the location information, is streamed to a remote computational device. When data collection completes, the stored data may be transmitted through a wired connection or by physically transferring a flash card to the target computational device.

In some embodiments, streamer module 553 formats images, video, audio and other data in a format for streaming to an application executing on a remote computational device via communication subsystem 529 or for storing it in memory 530. In some embodiments, streamer module 553 formats images, video, audio and other data in a format suitable for streaming to an Internet browser, for example, but not limited to, HTTP streaming, HTML, HTML5, RTSP, WebRTC. In some embodiments, streamer module 553 formats images, video, audio and other data with compression formats and/or format containers such as, but not limited to, JPG, JPG 2000, MPEG-4, H.264, H.265, AAC, PCM, G.711, G.726, and the like. In some embodiments a proprietary format is used, however the invention is not so limited.

In addition to streamer module 553, handle 320 may transmit data using a HTTP server 556. In some embodiments, HTTP server 556 responds to HTTP requests originating in a remote computational device.

File system module 567 controls how data is stored at least in part of memory 530. In some embodiments, file system module 567 stores data in a standard format such as FAT, NTFS, ext, or the like.

Figure 6A:
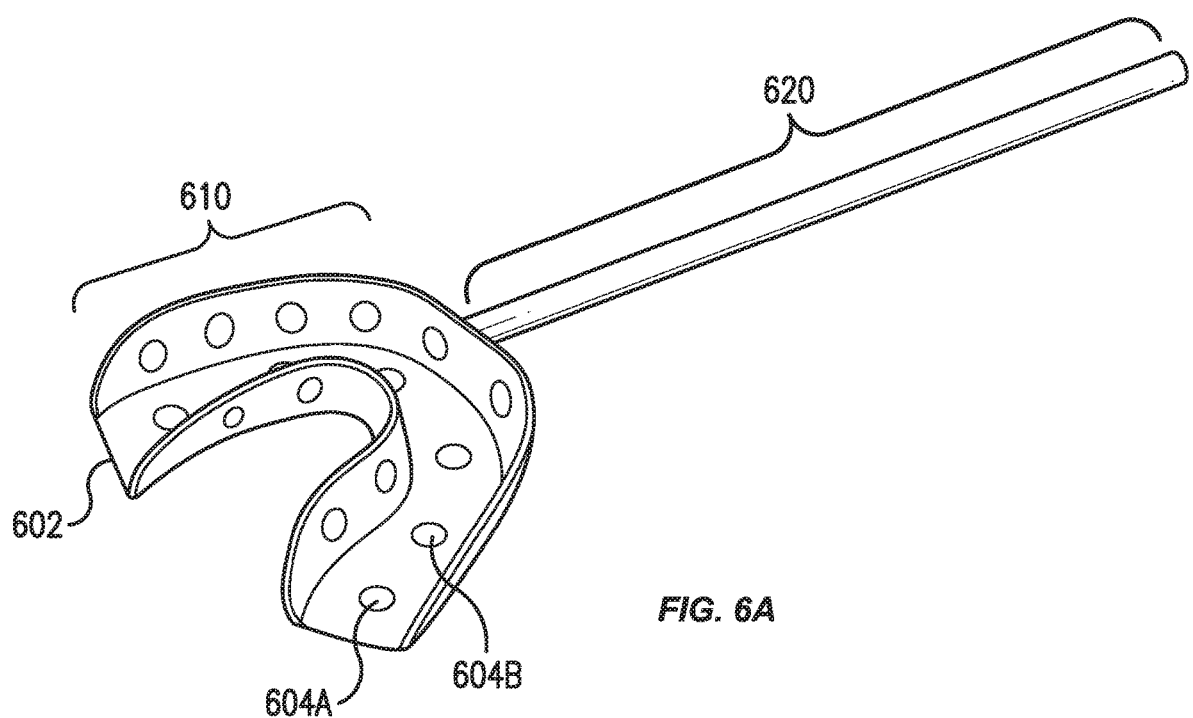
FIG. 6A is a diagram illustrating a dental tray imaging device.

As seen earlier, camera 300 of FIG. 5 includes a head 310 in the shape of a sphere. Such a sphere may enable producing a viewport space that allows an observer to rotate the view at any angle around a center, with the possible exception of the area where head 310 attaches to handle 320. Alternatively, other shapes of camera heads may provide more efficient capturing of immersive photographs in an intraoral environment producing a different viewport space. FIG. 6A is a diagram illustrating a dental tray imaging camera 600. Like camera 300, camera 600 includes a handle, labeled handle 620. However, instead of the sphere, the head 610 of camera 600 has the shape of a dental impression tray. The shape may, perhaps completely, enclose a patient's dental arch. The tray may have two pieces, one enclosing the superior dental arch and the other enclosing the inferior dental arch. The tray may be removable and may be one of several sizes available depending on the size of the patient's arch. The tray may be configured to enable a patient to bite down into the enclosures. In some embodiments, the shape of head 610 may be of half a tray, perhaps covering half of a dental arch.

When positioned over a dental arch, a health care provider may use the tray to capture images of a whole arch. The dental tray has openings 604A-B (or other type of passthrough) for light sources and image sensors. The light sources illuminate the patient's arch, and the image sensors capture photographic images of the patient's arch. The openings may be located at the internal area of the dental tray (the area which may be in contact with the enclosed teeth), and also at the external area (the area that may be in contact with cheek or tongue), so that the viewport space includes images of the dental arch being enclosed, and also, at least in part, other areas of the intra-oral environment.

Alternatively, perhaps for the purpose of reducing the amount of required image sensors, and thus reducing cost, the camera head may be of the shape of a section of an impression tray, thus having a "U" or horseshoe shape. For example, the "U" shape head may be positioned to cover one tooth, allowing the embedded image sensors to capture images of one the tooth from many angles simultaneously. Openings for image sensors and light sources may be on the interior of the "U" or horseshoe shape to capture photographic images of the tooth surfaces, for example the buccal, occlusal and lingual surfaces, and openings for image sensors and light sources may be on the exterior of the "U" or horseshoe shape to capture the surrounding intra oral environment. Naturally, a larger "U" shape head that covers more than one tooth may be used.

Figure 6B:
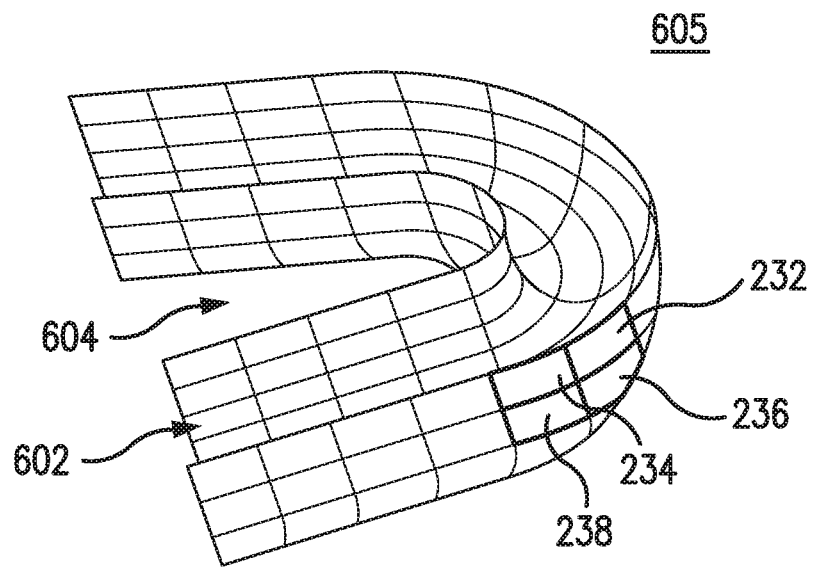
FIGS. 6B-C are diagrams illustrating an immersive photographic image of a dental tray imaging device and rendering it to a viewport.

The viewport space for presentation of perspectives of the immersive view may correspond to the shape of the camera head, as illustrated in FIG. 6B. FIG. 6B illustrates the alignment of images 605 captured with a tray-shape camera head 610. As discussed above for FIG. 2A, it includes pixels from images 232, 234, 236, and 238.

Alignment 605 may be of a shape resembling a trough, or half a tube, curved into a 3D dental arch shape. Alignment 605 includes an inner surface 602 and an outer surface 604. Inner surface 602 is the inner surface of the trough, and outer surface 604 is the outer surface of the trough. When head 610 encloses the inferior dental arch, photographic images captured from image sensors facing the patient's lower teeth may be mapped to an inner surface 602, and photographic images captured from image sensors facing the patient's upper teeth, and perhaps the cheek, may be mapped to an outer surface 604.

Figure 6C:
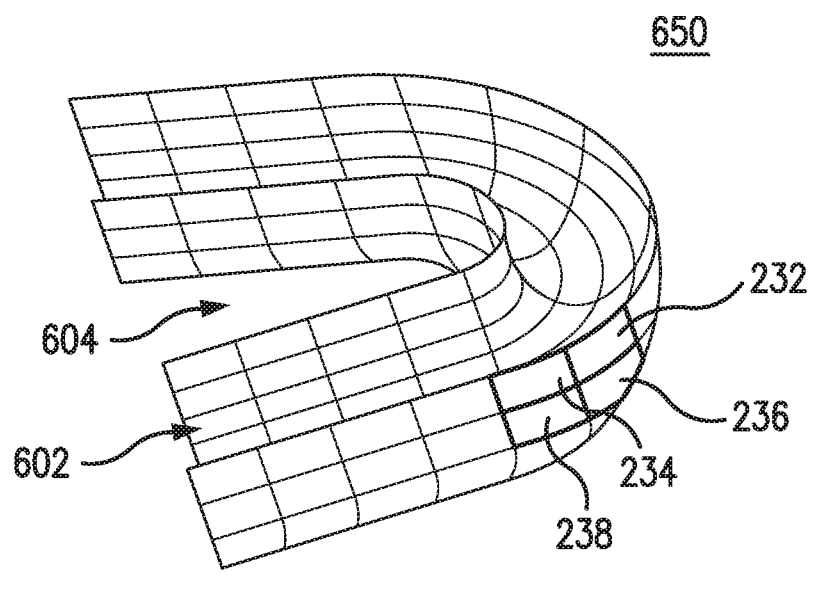
Figure 6C:
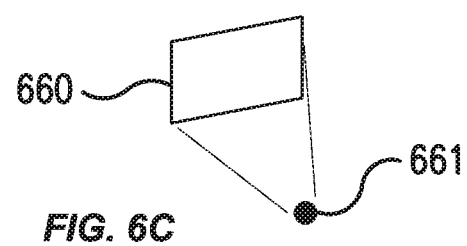

FIG. 6C shows an alignment 650 illustrating the geometry for rendering a viewport of such an immersive photograph. In alignment 650, the immersive photograph is rendered according to a virtual camera having viewport 660 and focal point 661. Unlike FIG. 2B, not all angles around the focal point 661 may render an image, since the focal point is not enclosed by alignment 650, thus some angles around the focal point are not included in the viewport space. An observer may, instead, move the focal point along the surfaces of alignment 650. Since frequently a health care provider is interested in observing this area, this limited control of viewport selection may be appropriate.

As described above for FIG. 2B, the ability of an observer to move a virtual camera thus selecting different viewports imparts a sense of perspective and depth on the rendered image.

Figure 7:
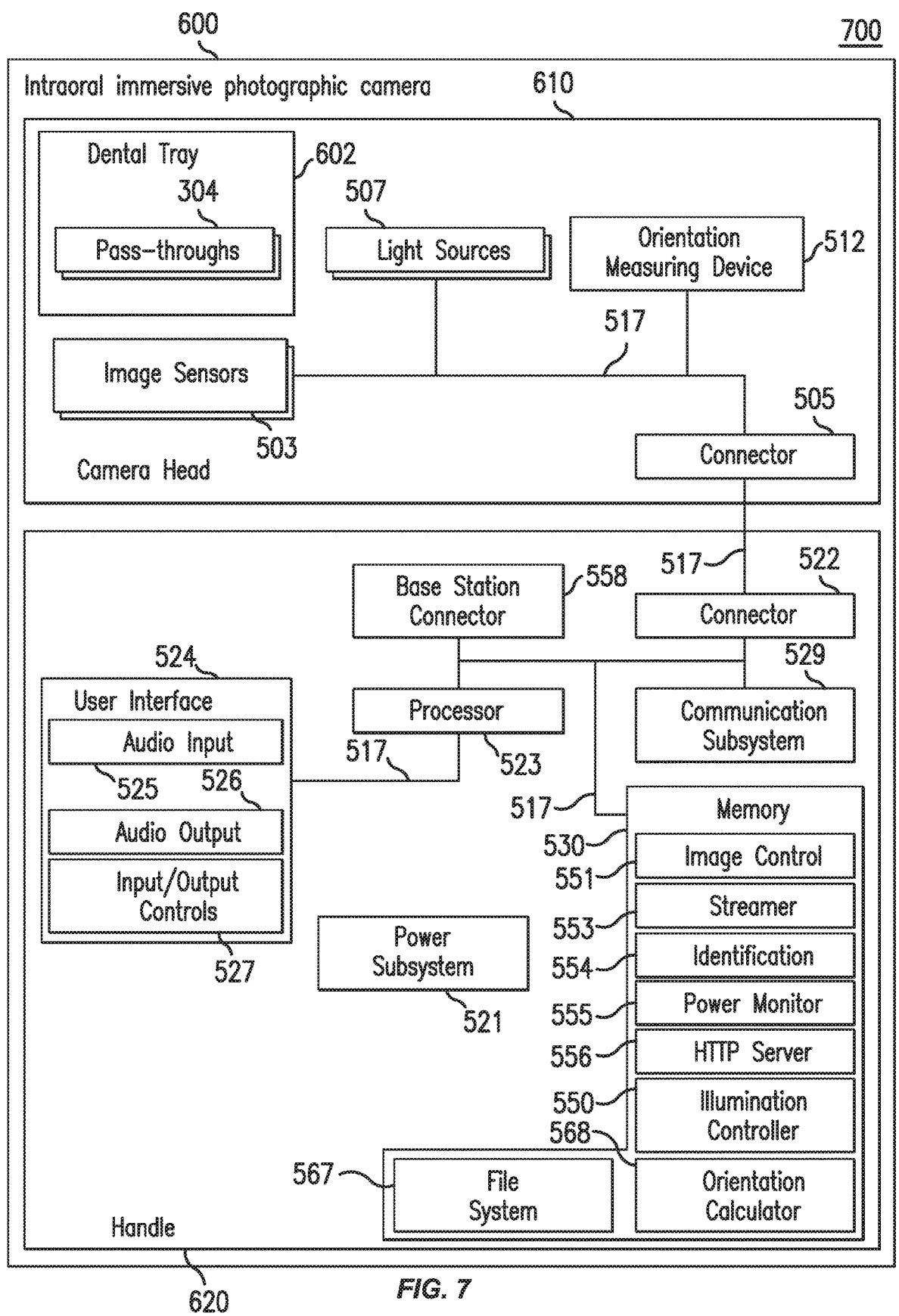
FIG. 7 is a system diagram of the dental tray imaging device.

FIG. 7 is a system diagram 700 of dental tray imaging device 600 illustrated in FIG. 6A. Intraoral immersive photographic camera 600 is similar to camera 300, except its camera head 610 may have a different shape. In particular, camera head 610 includes a dental tray 602 as described above with respect to FIG. 6A. Again, camera head 610 may be detachably connected to handle 620, which is similar to handle 320 described, for example, with respect to FIG. 5.

In this way, various devices are disclosed that enable capture of immersive photographs having different viewport spaces.

III. SYSTEM AND METHOD FOR GUIDING PLACEMENT OF ORTHODONTIC BRACKETS

Systems and the captured immersive photographs may be used to guide placement of orthodontic brackets, as illustrated in FIGS. 8-10 and 11A-B.

Figure 8:
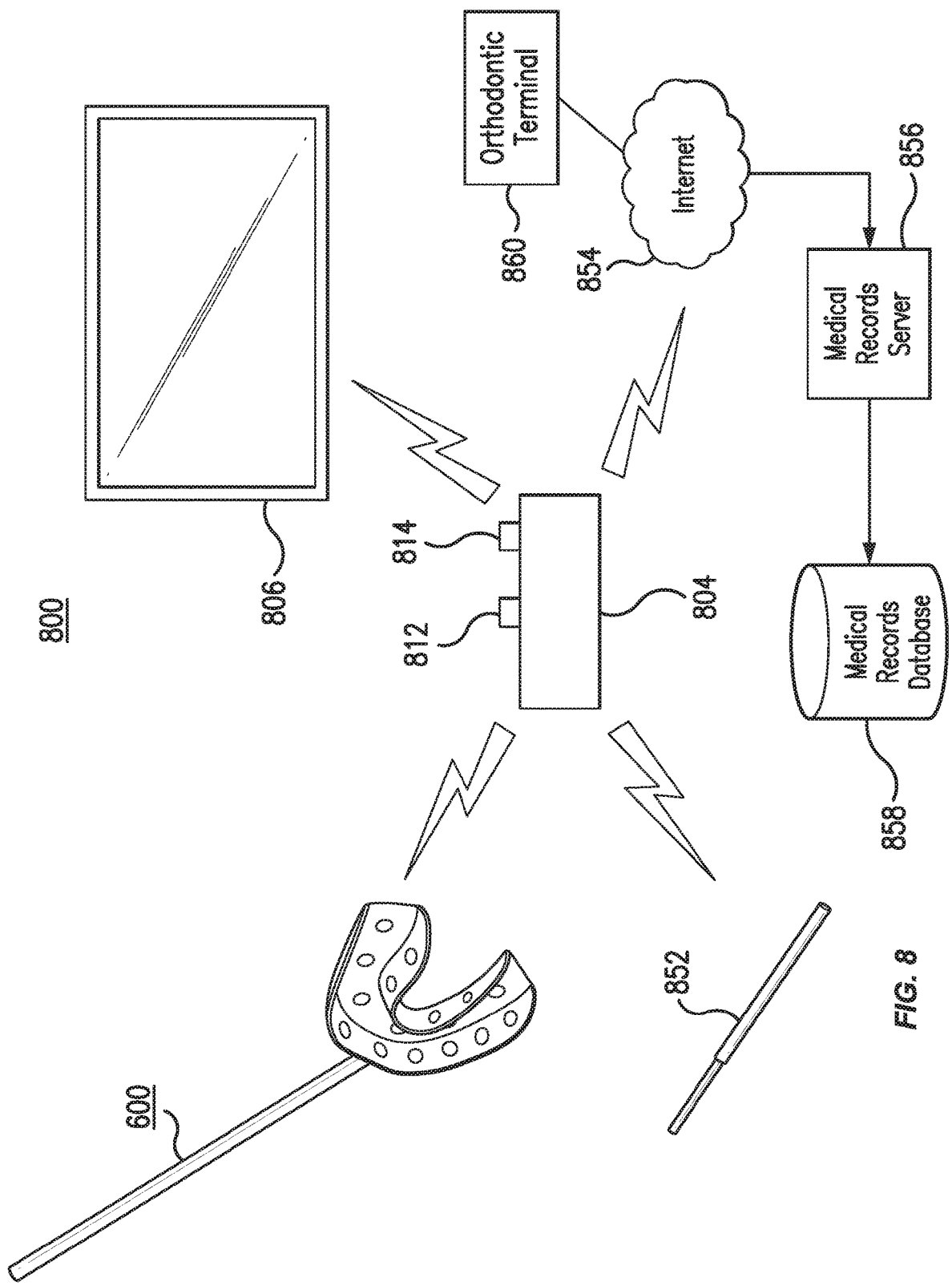
FIG. 8 illustrates a system for to generate immersive views and dental impressions, to determine the location to place orthodontic brackets using the generated immersive views, and to use the determined locations to guide placement of the orthodontic brackets.

FIG. 8 illustrates an architecture diagram of a system 800 for generating immersive photographic models including dental measurements, determining the location to place orthodontic brackets using the generated immersive views and dental measurements, and using the determined locations to guide placement of the orthodontic brackets.

System 800 includes various components that may be located within a dental office, including, for example, the room in which a patient is treated. System 800 includes immersive camera device 600, an intraoral camera 852, and a tablet 806, each of which may be in wireless communication, such as Wi-Fi, with each other or with a base station 804. Base station 804 includes cradles 812 and 814 for immersive camera device 600 and perhaps for intraoral camera 852. Intraoral camera 852 may be integrated into a dental mirror as described, for example, in U.S. Pat. No. 9,629,532, incorporated by reference herein in its entirety.

Base station 804 allows multiple camera devices 600 and 852 to be used in the same room. For example, an assistant may use one mirror on a patient while a dentist uses another on the same patient. Base station 804 includes multiple cradles 812 and 814 to allow multiple devices to dock.

Once a health care provider is no longer using devices 600 and 852, he may place them on cradles 812 and 814. When devices 600 and 852 are docked with cradles 812 or 814, base station 804 may charge them. Also, as described above, when docked with cradles 812 or 814, devices 600 or 852 may calibrate their gyroscope and accelerometer, or transfer data stored in their internal memory.

Base station 804 also provides for communication with devices 600 and 852. In particular, camera devices 600 and 852 transmit images, location or other data to base station 804, which transmits information for display on tablet 806. Base station 804 may act as a Wi-Fi router and provide network routing and address information to camera devices 600 and 852. For example, immersive camera device 600 may wirelessly transmit its location, and perhaps a partial representation of the images or video being captured, while the full set of images or video is stored in memory. This may allow tablet 806 to display an indication for which of the intraoral areas of the patient's mouth were already captured at present and which were not, without overflowing the transmission bandwidth.

Base station 804 is connected to medical records server 856 via one or more networks 854, such as the Internet. Base station 804 may be connected to the Internet either through a wireless or wired LAN in the dental office. Server 856 is a computerized process adapted to run in one or more remote computers. Server 856 may, for example, be a cloud server. Server 856 is further connected to an archival medical records database 858. Medical records database 858 stores medical record information, including imagery information collected from cameras 600 and 852 used to generate immersive photographs and dental impressions.

Orthodontic terminal 860 is a terminal that an expert can use to determine placement of orthodontic brackets based on immersive photographs and dental measurements. Orthodontic terminal 860 is illustrated in greater detail in FIG. 9.

Figure 9:
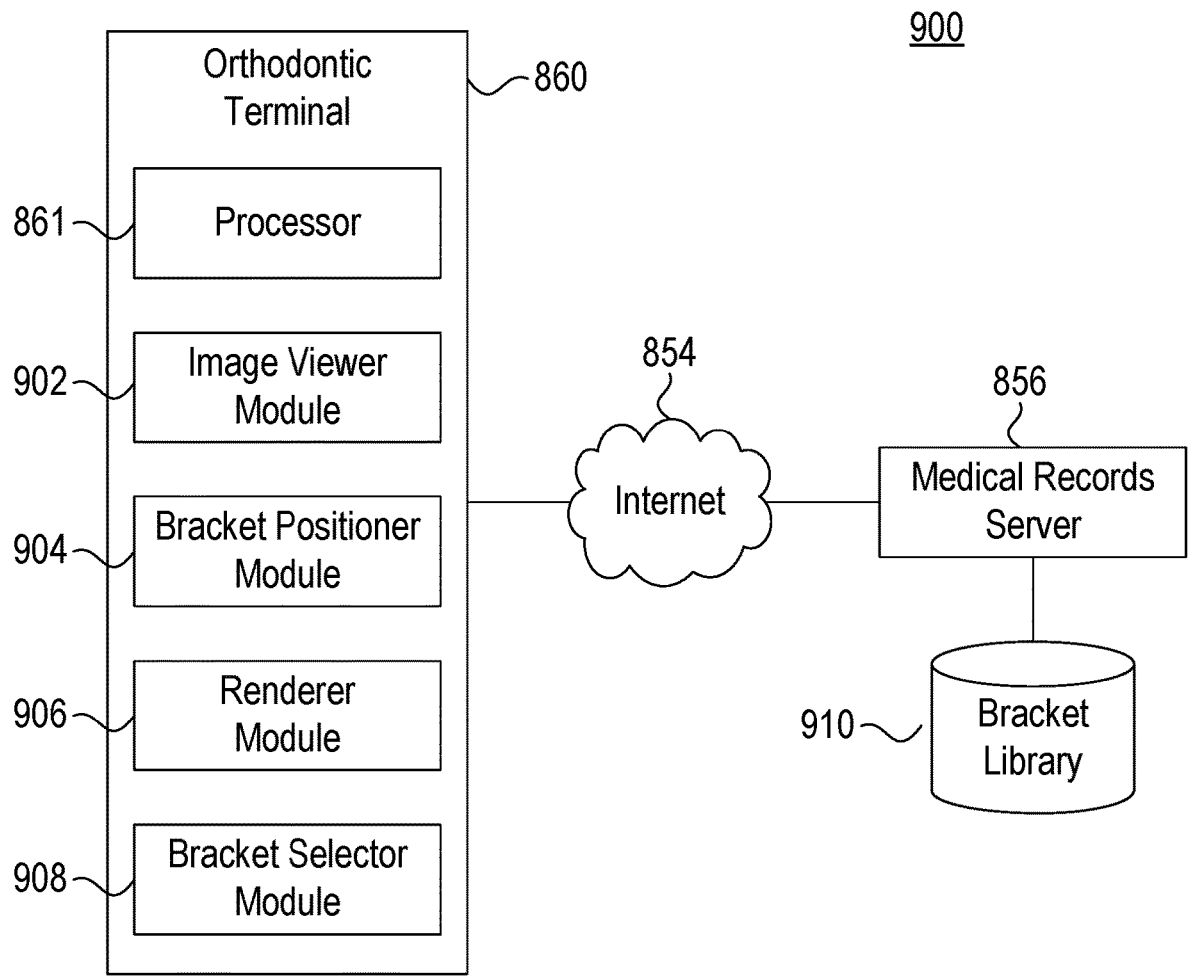
FIG. 9 illustrates a terminal used by a healthcare practitioner determine a location to place an orthodontic bracket using immersive views.

FIG. 9 illustrates a system 900 including orthodontic terminal 860 used by an expert practitioner to determine a location to place an orthodontic bracket using immersive views and dental measurements of a patient's teeth. An expert practitioner may be, for example, a determining placement location as a service for another practitioner, or may be an orthodontist preparing for a patient's session. Orthodontic terminal 860 is in communication with medical records server 856 over one or more networks 854, such as the Internet. In an embodiment, orthodontic terminal 860 is a web-based application hosted with the medical records server 856. Orthodontic terminal 860 includes a processor 861, an image viewer module 902, a bracket position module 904, a renderer module 906, and a bracket selector module 908.

Before positioning the bracket, bracket selector module 908 may select the orthodontic bracket to be used from a plurality of different types of orthodontic brackets stored in a bracket library 910. Bracket selector module 908 may connect to bracket library 910 by connecting to medical records server 856 via networks 854. Each type of orthodontic bracket is designed for a different tooth anatomy or designed to achieve a different desired orthodontic goal. Bracket selector module 908 may select the orthodontic bracket based on an input from the health care practitioner. Alternatively, bracket selector module 908 may analyze imagery data (or request such analysis from server 856) to determine a tooth number (e.g. 1st Bicuspid) and possibly the size and shape of the patient's tooth and use these values to select a bracket.

Image viewer module 902 is configured to receive an input indicating a location selected by a health care professional on an image rendered to a viewport of an immersive view. In an example operation, image viewer module 902 may download an immersive view for a patient from medical records server 856. Then, image viewer module 902 may render a perspective of the immersive view to a viewport for display. On the viewport, the health care professional selects a position to place an orthodontic bracket on a patient's tooth. In an alternative, image viewer module 902 determines the desired viewport, and requests a rendering of the viewport from medical records server 856. The received image, corresponding to the viewport rendering, is then displayed.

Based on one or more selected positions in one or more viewports, bracket positioner module 904 determines the corresponding position on the immersive photographic model. In an embodiment, bracket positioner module 904 may extend a ray from a focal point of a viewport at a direction determined based on the input. Then, bracket positioner module 904 may determine a location along the ray at an estimated distance between the focal point and the perceived patient's tooth. Alternatively, bracket positioner module 904 may determine an intersection between various rays extended from two or more focal points of two or more viewports based on selections that the health care provider made on the viewports. The intersection indicates a position in three-dimensional space, relative to positions of other elements of the immersive photographic model, to place a 3D model of an orthodontic bracket on the perceived position of the patient's tooth. This is illustrated, for example, in FIGS. 1A-B. Bracket positioner module 904 may also determine a scaling for the simulated bracket to fit the dimensions of the perceived patient's tooth based on dental measurements. Bracket positioner module 904 may further position the 3D model of the orthodontic bracket to allow for spacer between the model of the orthodontic bracket and the perceived position of the of the patient's tooth.

To preview how the bracket would appear if placed at the selected position, image viewer module 902 may superimpose a 3D model of the orthodontic bracket onto the immersive view photographic model. A rendered image through a viewport of the combined model illustrates to the health care professional the location to select for placement of the orthodontic bracket on the patient's tooth. Image viewer module 902 may receive the combined image from renderer module 906.

Renderer module 906 is configured to render a perspective of a 3D model of the orthodontic bracket combined with the immersive view photographic model to generate the image of the view of patient's mouth and the superimposed orthodontic bracket. Renderer module 906 may render the 3D model of the orthodontic bracket to rest in the position determined by bracket positioner module 904 in an appropriate reference frame such that the rendered image illustrates the orthodontic bracket positioned to attach to the patient's tooth from the desired perspective of the immersive view. Health care practitioners may then input controls to adjust the position or scaling of the simulated bracket if they see fit. Renderer module 906 may also render a spacer between the model of the orthodontic bracket and the image of the patient's tooth.

In this way, system 900 enables a health care practitioner to determine placement of an orthodontic bracket using immersive views and dental measurements. The operation of system 900 is illustrated further in FIG. 10.

Figure 10:
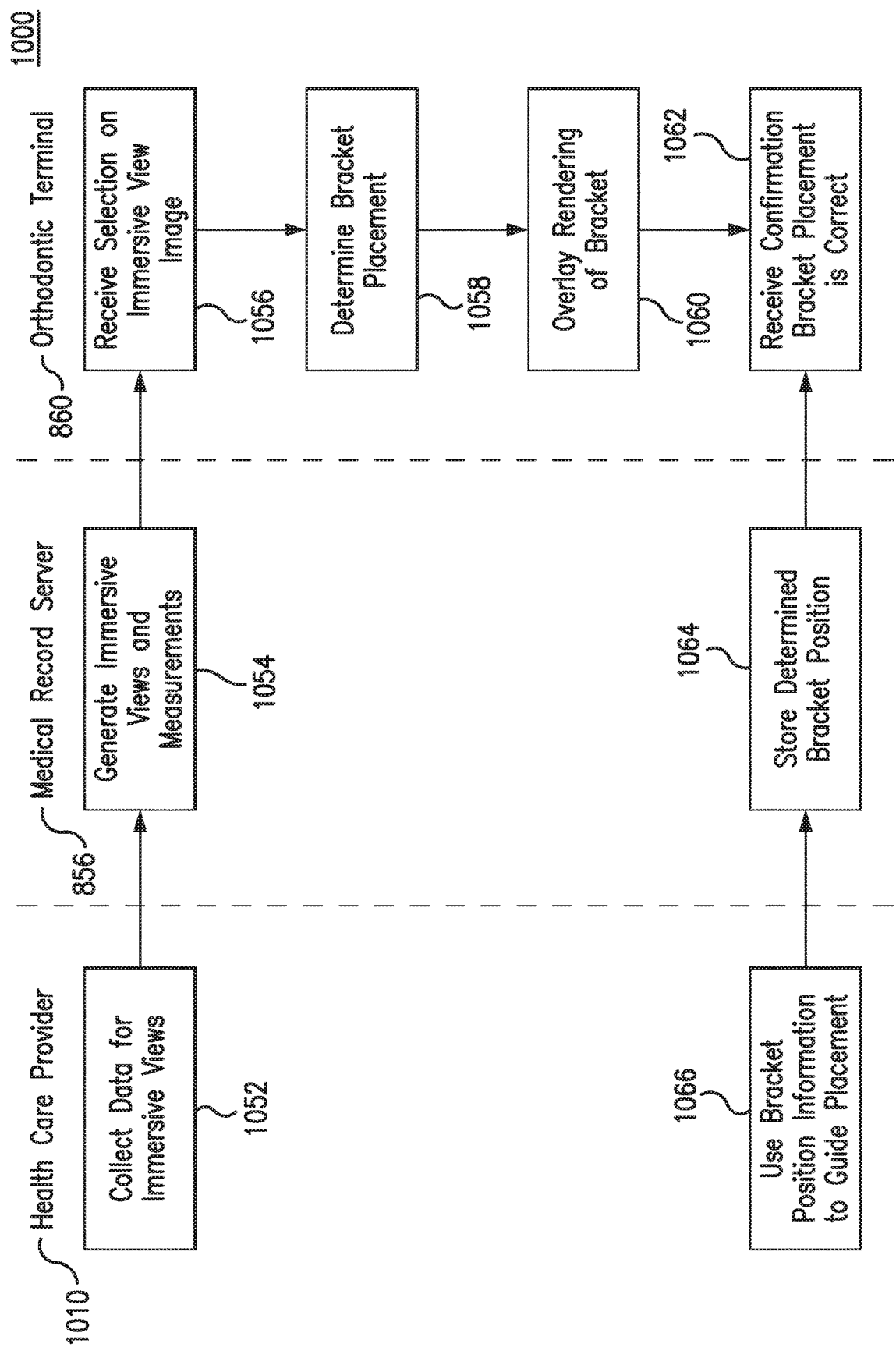
FIG. 10 is a flowchart illustrating a method for determining the location to place an orthodontic bracket using immersive views.

FIG. 10 is a flowchart illustrating a method 1000 for determining the location to place an orthodontic bracket using immersive views and dental measurements.

Method 1000 begins at a step 1052 when a health care provider 1010 collects imagery and position data to generate immersive views and dental measurements. That data may be collected using the devices described earlier with respect to FIGS. 3 and 6A. That data is eventually transmitted to medical records server 856.

At step 1054, medical records server 856 uses the collected imagery data and associated position data to generate at least one immersive view and perhaps also measurements of the intraoral environment of the patient's mouth. Medical records server 856 provides the immersive view, or alternatively renderings of perspectives of the immersive view, and possibly dental measurements to orthodontic terminal 860.

At step 1056, orthodontic terminal 860 receives an input indicating a location selected by a health care professional on a rendered viewport of an immersive photographic model. The input indicates a position to place an orthodontic bracket on a patient's tooth, as discussed in FIG. 9.

At step 1058, orthodontic terminal 860 determines an initial bracket position on the patient's tooth based on the locations on one or more photographs that were selected by the health care professional.

At step 1060, orthodontic terminal 860 superimposes a synthetic 3D model of the orthodontic bracket onto the immersive photographic model. The outcome illustrates to the health care professional a placement of the orthodontic bracket on the patient's tooth.

Based on the superimposed model, the health care professional indicates whether the bracket placement is correct at step 1062. If the bracket placement is incorrect, the health care professional can make adjustments until it is correct. If the bracket placement is correct, orthodontic terminal 860 transmits to medical records server 856 the position within the immersive view photographic model to place the orthodontic bracket. Medical records server 856 stores the placement information for the bracket at step 1064.

Finally, at step 1066, health care provider 1010 can use the stored bracket position information to guide placement of the bracket. For example, health care provider 1010 may view a monitor that indicates where the bracket should be placed on a patient's tooth as illustrated in FIG. 11A.

Figure 11A:
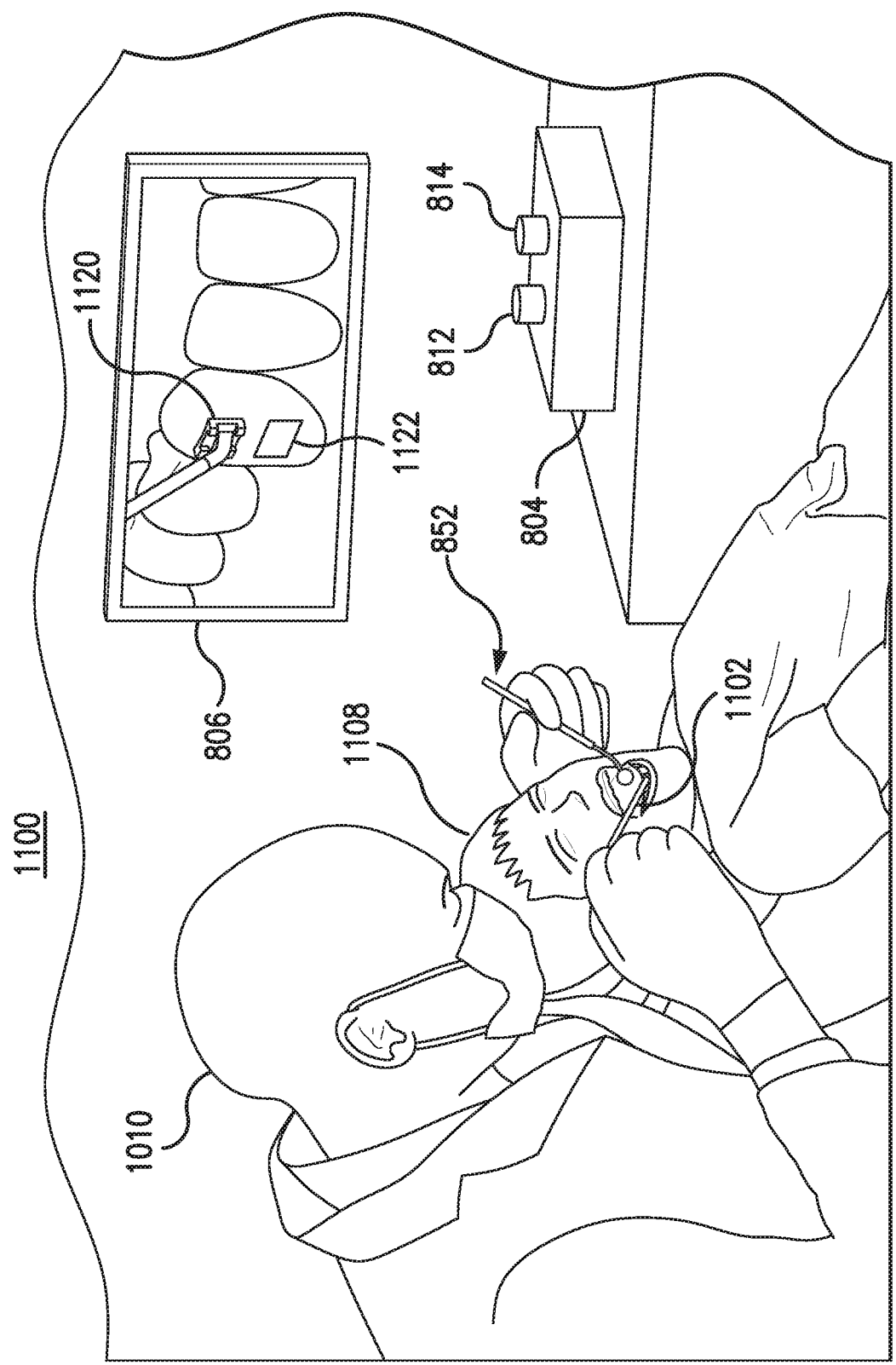
FIGS. 11A-B illustrate an in-room system to guide placement of the orthodontic brackets.

FIG. 11A illustrates a room 1100 of a dental office including a system for guiding placement of orthodontic brackets. Room 1100 shows a health care provider 1010 utilizing a bracket placement tool 1102 to place a bracket on a tooth of a patient 1108.

Base station 804 may send a message to tablet 806 to instruct the health care provider 1010 as to which type of bracket is to be used. Bracket placement tool 1102 may enable health care provider 1010 to grasp an orthodontic bracket, position it on patient 1108's tooth, and release the bracket once it is set in the desired location.

Additionally, health care provider 1010 is using intraoral camera 852 to capture video of the patient's mouth. Tablet 806 shows the video captured from intraoral camera 852. In particular, the video shows an orthodontic bracket 1120 that health care provider 1010 is currently positioning on patient 1108's tooth. Superimposed on the video is a marking 1122 indicating the position that was previously selected as the location on the patient's tooth to place the bracket. Marking 1122 guides the health care provider 1010 in placing the orthodontic bracket on the patient 1108's tooth. Video may be streamed from camera 852 to tablet 806 through base station 804 and base station 804 may superimpose marking 1122 before the video is streamed to tablet 806. In this way, a dentist or assistant may observe the rendered images that result from the rendering of the images captured at camera 852 and the superimposed marking 1122 as an aid to place a bracket in the correct location on the patient's tooth. Thus, a health care provider have an improved visual guidance towards the goal of correctly placing bracket 1120. Instead of solely watching a bracket inside a patient's mouth from a distance that is large when compared to the dimensions of the bracket, a health care provider can glance at the larger display showing a magnification of the video, enabling to more accurately asses how close the current bracket placement is when compared to the target placement. In an embodiment, marking 1122 is a rendering of a synthetic 3D model of a bracket.

In an embodiment, once a health care provider has placed the orthodontic bracket on the patient's tooth, camera 852 may capture an assessment image of the patient's tooth. Base station 804 may determine where, in the assessment image, the orthodontic bracket is located. Base station 804 may compare the orthodontic bracket's determined location to the desired position as indicated by marking 1122. When the orthodontic bracket's determined location is determined not to correspond to the position indicated, base station 804 may send a message to alert the health care professional, and may even guide towards what direction and how much the bracket should move.

Alternatively, tablet 806 displays two videos, one is the video being captured by camera 852, and the other is a rendering of corresponding viewports of the immersive photographic model superimposed with the synthetic 3D model of the bracket. The motion of camera 852 may control the selection of viewports, so that corresponding images are continuously displayed. A health care provider 1010 may place the bracket on a tooth while continuously comparing the videos being displayed until he is satisfied that the placement of the bracket on both images match.

In this way, embodiments provide placement information for each tooth separately, without the inaccurate positioning of a single tooth bonding jig.

If a bracket falls or has to be removed, health care provider 1010 may use the system to replace a bracket. Even if a tooth already shifted in the mouth, its shape remains. The simulated bracket still shows the bracket position that was selected by the expert, and can be used as reference for replacement.

Moreover, the acquisition of another dental immersive model is straightforward, and a dentist may acquire one just prior to repositioning, thus using the most recent model as a reference. Thus, immersive photographs can be acquired among visits of the patient to the dental office. These can be subsequently sent to an expert for assessment of progress and, if repositioning or replacement are necessary, the expert can follow the same process as with the initial placement, only now the aligned images contain also real brackets attached to teeth.

Figure 11B:
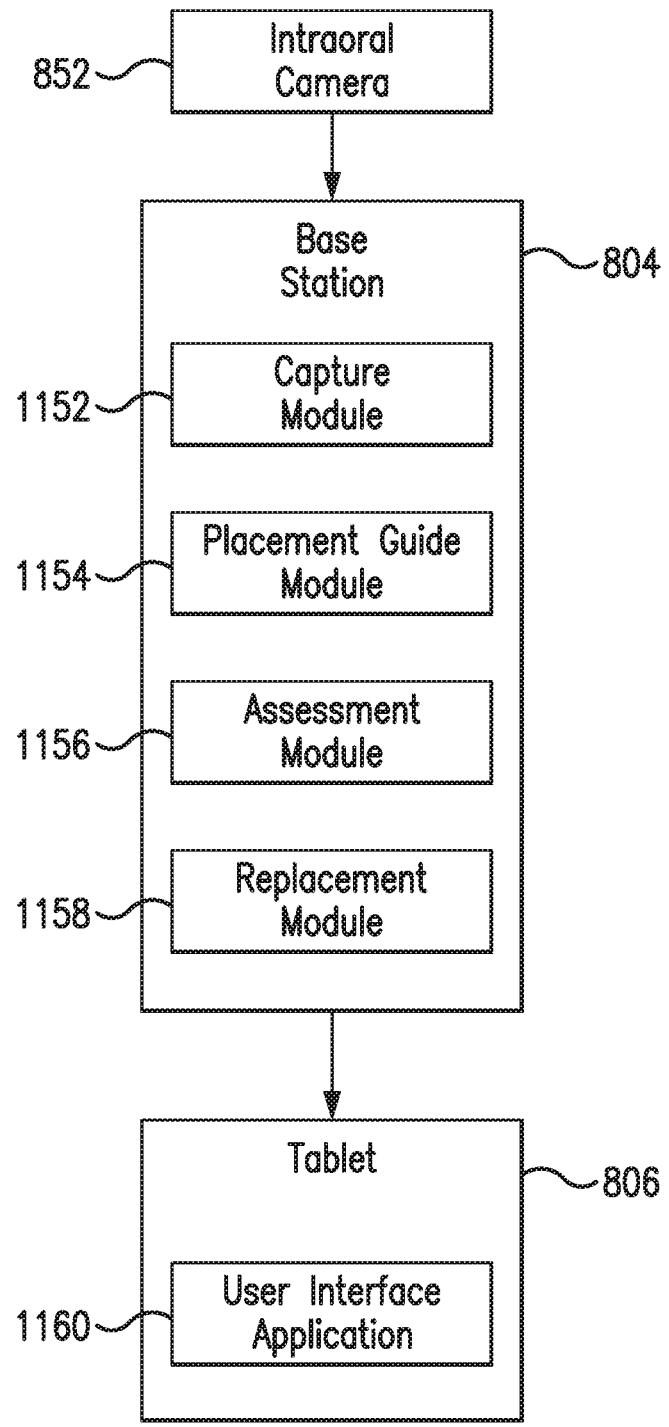

FIG. 11B is a diagram 1150 illustrating components of in-room system 1100 in FIG. 11A in greater detail.

As described above, intraoral camera 852 streams video to base station 804. Base station 804 includes a capture module 1152, a placement guide module 1154, an assessment module 1156, and a replacement module 1158.

When a health care provider is placing the orthodontic bracket, capture module 1152 captures video of the patient's tooth by receiving and possibly buffering the video received from intraoral camera 852. Capture module 1152 may also capture an assessment image of the patient's tooth for assessment module 1156.

Placement guide module 1154 superimposes markings on the video indicating the desired position for the bracket. The desired position may, for example, be retrieved from a medical records server (not shown). By superimposing markings, placement guide module 1154 guides the health care provider in placing the orthodontic bracket on the patient's tooth. Placement guide module 1154 may superimpose the marking onto a video captured from an intraoral camera to guide the health care provider. In another embodiment, placement guide module 1154 may generate another video to display side-by-side with the video collected from the intraoral camera. To generate the other video, placement guide module 1154 may select a viewport to correspond to the orientation of the intraoral camera. The marking may be superimposed on a rendering of the immersive photographic model from the perspective of the viewport. This may result in a more accurate guide for the health care provider. For example, this approach may be more tolerant of errors in determining the position of the intraoral camera.

Assessment module 1156 determines whether a bracket is correctly placed. To determine whether the bracket is correctly placed, assessment module 1156 determines where, in an assessment image, an orthodontic bracket is located. Then, assessment module 1156 compares the orthodontic bracket's determined location to the desired position to place the orthodontic bracket on the patient's tooth which was retrieved from the medical records server. When the orthodontic bracket's determined location is determined not to correspond to the desired position, assessment module 1156 sends a message to alert the health care professional, perhaps also indicating the direction and shift required for the bracket to arrive at the desired location.

If the orthodontic bracket has become detached after the patient's tooth has moved, replacement module 1158 aids the health care provider in setting the system to compensate for a shift of a tooth. When a bracket is to be replaced, it is possible that the immersive view stored in the medical records server is not up to date, thus does not reflect the change in position or rotation of the tooth being treated. Replacement module 1158 allows a health care provider to determine a shift to the virtual camera, so that the selection of perspective of the particular tooth being treated as applied to the immersive view will correspond to the view from intraoral camera 852. Following this setup, it is possible that the perspectives of other teeth will not correspond. Placement guide module 1154 can superimpose markings and assessment module 1156 can send alert messages to ensure the bracket is replaced in a similar location on the patient's tooth.

Tablet 806 executes a user interface application 1160, which is in wireless communication with base station 804. User interface application 1160 is capable of displaying to a patient images collected from the image sensor and processed by base station 806.

In embodiments, some of the modules may operate, at least in part, in a remote computer, such as a cloud computer.

In this way, embodiments guide the placement of orthodontic brackets using immersive views and digital dental impressions.

IV. SYSTEM AND METHOD FOR GENERATING IMMERSIVE VIEWS AND DENTAL IMPRESSIONS

Figure 12:
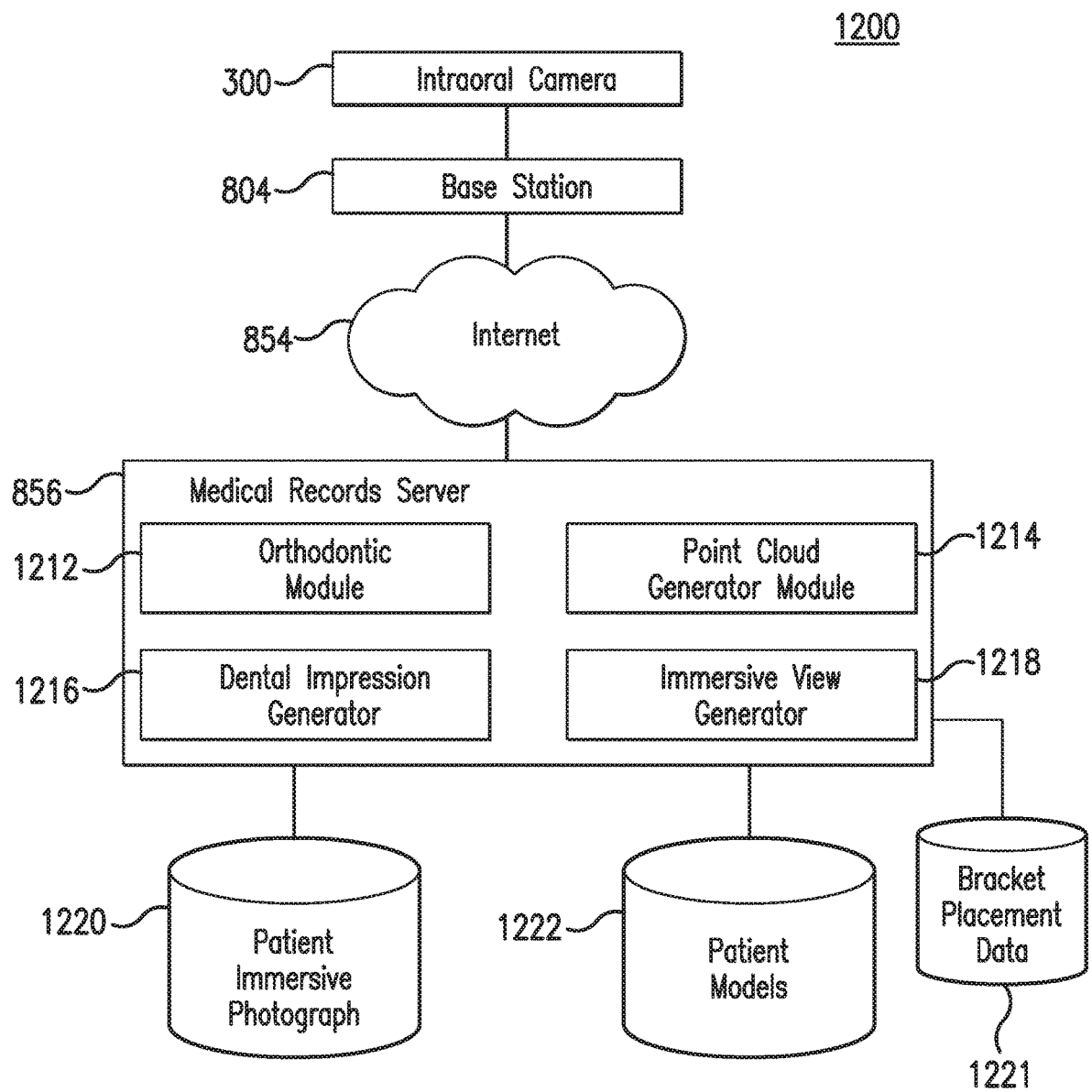
FIG. 12 illustrates a system for generating immersive views and digital impressions from imagery data.
Figure 13A:
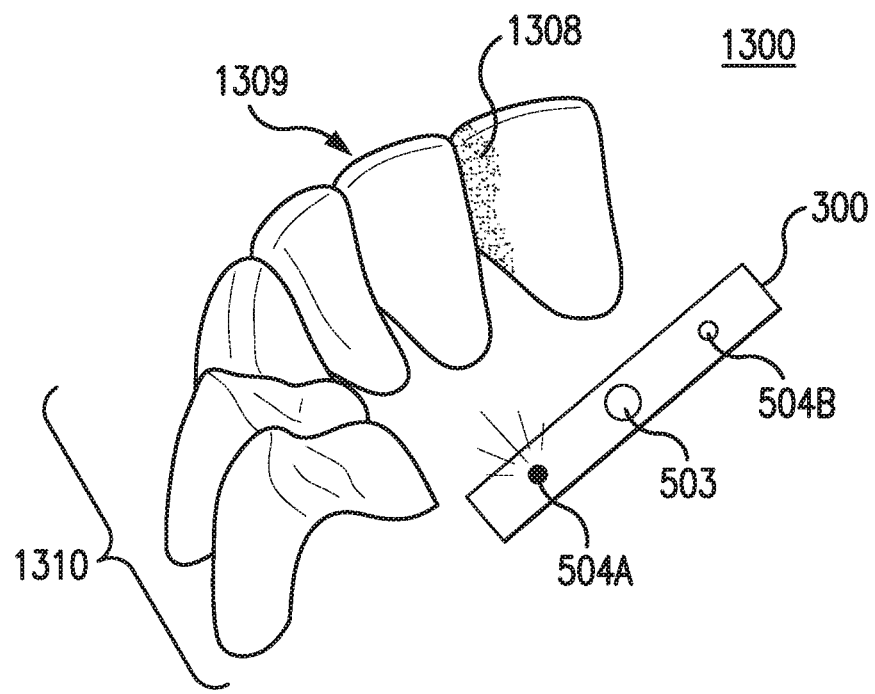
FIG. 13A-B illustrate using shape-from-shadow to determine a three-dimensional model of an intraoral environment.
Figure 13B:
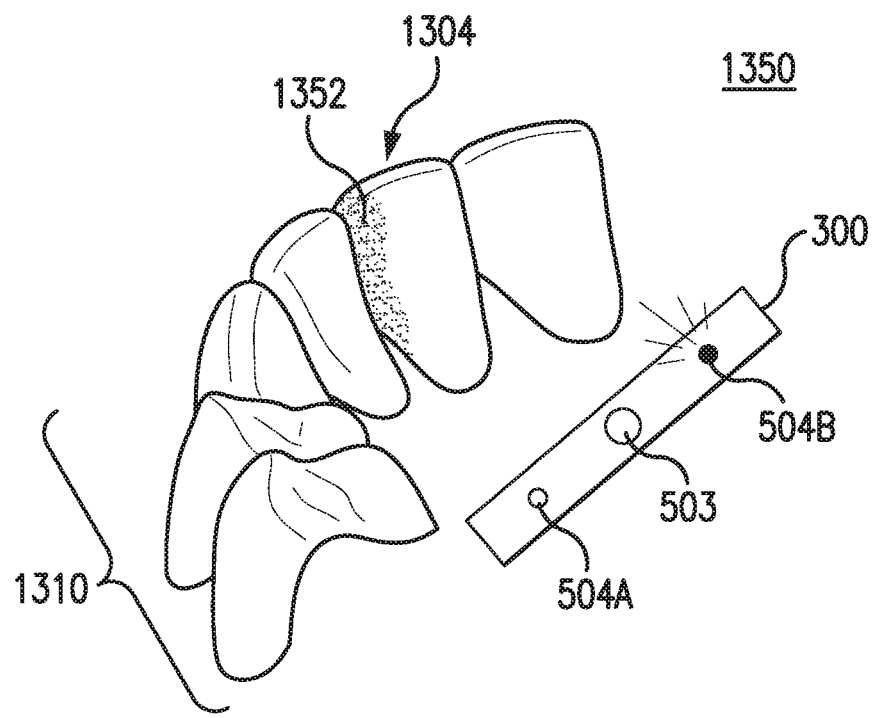

Systems and methods that generate immersive views and digital dental impressions from imagery data are described with respect to FIGS. 12 and 13A-B. Generating the dental impression or immersive views may require significant computing power. For example, appropriately stitching a large number of 2D images into one immersive view, determining dental measurements, and determining intraoral surfaces to produce an impression may require significant memory or processing power. To deal with this, embodiments separate the immersive photographic model and impression generation from the data acquisition. In particular, the data may be acquired using a camera device and base station in a dental office, and the base station may transmit the data to a remote server for processing as illustrated in FIG. 12.

FIG. 12 illustrates a system 1200 for generating immersive photographic models and dental impressions from imagery data. FIG. 12 illustrates a system 1200 with a server to generate immersive photographic models and dental impressions. Like the system in FIG. 8, system 1200 includes intraoral immersive photographic camera 300 and base station 804, which is connected by one or more networks 854 to medical records server 856.

The medical records server 856 includes an orthodontic module 1212, a point cloud generator module 1214, a dental impression generator module 1216, and an immersive photographic model generator module 1218. Medical records server 856 is also coupled to a patient immersive photograph database 1220 and patient model database 1222.

Medical records server 856 receives (i) a plurality of photographs of the interior of the patient's mouth, (ii) associated position information for the respective photographs, and (iii) information describing how the respective photographs were illuminated. The plurality of photographs are collected from one or more image sensors affixed to an intraoral immersive photographic camera 300 each overlapping at least in part with another one of the plurality of photographs. Once collected, they are stored, together with their respective position information in patient immersive photograph database 1220.

Orthodontic module 1212 stores and maintains bracket placement data in bracket placement database 1221. The bracket placement data may be the location selected by an expert to place an orthodontic bracket on each tooth.

Point cloud generator module 1214 generates a point cloud from position information and aligns it to point clouds generated during previous dental sessions, to allow the alignment of images captured at different dental sessions. Point cloud generator module 1214 may generate a point cloud by analyzing positions of image sensors when images are captured, identifying positions that correspond to meaningful locations within the dental office's room, for example the area where the patient's mouth may be found during treatment, detecting features in the images, identifying common features between images, and triangulating the position of those features in three-dimensional space using the known orientation information of the cameras.

Immersive photographic model generator module 1218 determines features in the overlapping portions that match between two or more photographs. Based on associated position information for the respective photographs and the matching features, immersive photographic model generator module 1218 maps the plurality of photographs onto the appropriate shape for example to a sphere as described for FIG. 2A-2B or to a shape resembling a trough, as discussed for FIG. 6B-6C or to a difference shape as appropriate for the design of the immersive camera being used. Then, immersive photographic model generator module 1218 stitches the plurality of photographs of the interior of the patient's mouth into an immersive photographic model representing the captured images so that a mapping is created between positions in the patient's mouth and a viewport space. For producing a stereo immersive photograph, immersive photographic model generator module 1218 stitches two immersive views at an horizontal displacement, so that the visual information of both may be combined to stereo images. The horizontal axis is selected to be parallel to the horizontal plane of the reference 3D space, which, for example, may be parallel to the base of the virtual camera. In embodiments, immersive photographic model generator module 1218 transforms the perspective of two images, captured by two embedded cameras that are at an angle to each other, so that after the transformation the images seem to have been captured by two cameras that have the center of their field of view parallel to each other.

Once generated, immersive photographic model generator module 1218 stores the immersive model into patient model database 1222. Patient model database 1222 stores historical patient model information including historical immersive images of a patient's mouth. Patient model database 1222 may correlate portions of the immersive images with each other and with other images of a similar area of the patient's mouth. The other images may, for example, be x-ray images. Once generated and stored, the images rendered to viewports of the immersive view may be retrieved for display.

Not only can medical records server 856 generate an immersive view, medical records server 856 can also generate a dental impression. To generate a dental impression, medical records server 856 uses dental impression generator 1216 that determines points on the surface of objects in the mouth using feature matching and triangulation. Dental impression generator 1216 may also use image analysis techniques, including the shape from shadow techniques, discussed below. From the surface points, dental impression generator 1216 generates a dental impression of the patient's mouth. The dental impression may be a 3D mesh fit to the surface points.

In one embodiment, a structured-light may be used to generate dental impression information. Camera 300 projects light patterns while capturing images, thereafter the shape of the light as appearing on objects in an image is analyzed for measuring the 3D shape of the object. For example, the camera 300 may project light in a striped pattern. The light stripes tend to follow the curvature of the object they illuminate. By analyzing how the stripes appear on intra-oral objects in images captured by the camera, information on the surfaces of the objects may be determined.

FIGS. 13A-B illustrate determining a shape from a shadow cast by objects in the patient's mouth itself to determine a 3D model of an intraoral environment.

In particular, FIGS. 13A-B are diagrams illustrating how varying illumination from the intraoral camera can provide information on the 3D shape of a patient's teeth. FIG. 13A shows a diagram 1300 with a camera 300. Camera 300 has one or more image sensors 503 and a plurality of light sources 504A-B. Light sources 504A-B emit light from different openings in camera 300. Camera 300 is positioned to capture images of a patient's teeth 1310, in particular a tooth 1309.

In diagram 1300, light source 504A is illuminated, while light source 504B is not. Because of the varying illumination, tooth 1309 casts a shadow 1308. Image sensor 503 captures an image, including both tooth 1309 and shadow 1308. From the image, information about tooth 1309's 3D shape can be determined. In particular, brightness of the image can be analyzed to determine where shadow 1308 is located. The location of an image that occupies shadow 1308 is obscured by the 3D shape of teeth 1310 from the perspective of light source 504A, while the remainder of the image is not.

FIG. 13B shows a diagram 1350 illustrating camera 300 illuminated differently from diagram 1300 in FIG. 13A. In diagrams 1300 and 1350, camera 300 has substantially the same position and orientation with respect to teeth 1310. In diagram 1300, light source 504A is illuminated while light source 504B is not. But in diagram 1350, the opposite is true: light source 504B is illuminated while light source 504A is not. The different illumination casts a different shadow 1352 on tooth 1304. Again, from shadow 1352, shape information is determined. The location of an image that occupies shadow 1352 is obscured by the 3D shape of teeth 1310 from the perspective of light source 504B, while the remainder of the image is not.

Illumination between the various light sources may vary quickly, too quickly for the human eye to detect. As the illumination varies, shape information may be aggregated to generate a mesh of the surface points representing the surface of a patient's mouth, and in particular of teeth 1310. Additionally or alternatively, the light sources may emit light outside the visible spectrum, such as infrared light. And the shadows detected may be shadows in this invisible light spectrum.

V. CONCLUSION

The databases and libraries disclosed herein may be any stored type of structured memory, including a persistent memory. In examples, this database may be implemented as a relational database or file system.

Each of the processors, modules, terminals, and applications in for example FIGS. 5, 7, 8, 9, 11B, and 12 may be implemented in hardware, software, firmware, or any combination thereof implemented on a computing device. A computing device can include, but is not limited to, a device having a processor and memory, including a persistent, non-transitory memory, for executing and storing instructions. The memory may tangibly embody the data and program instructions. Software may include one or more applications and an operating system. Hardware can include, but is not limited to, a processor, a memory, and a graphical user interface display. The computing device may also have multiple processors and multiple shared or separate memory components. For example, the computing device may be a part of or the entirety of a clustered or distributed computing environment or server farm. Any of the components could be located on a head or a handle of an immersive camera.

Identifiers, such as "(a)," "(b)," "(i)," "(ii)," etc., are sometimes used for different elements or steps. These identifiers are used for clarity and do not necessarily designate an order for the elements or steps.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for positioning orthodontic brackets, comprising:
   (a) receiving, by at least one processor, an input indicating a location selected on an image by a health care professional to indicate a position to place an orthodontic bracket on a patient's tooth, wherein the image is rendered with respect to a viewport mapped onto an immersive photographic model of a patient's mouth;
   (b) extending, by the at least one processor, a ray from a focal point of the viewport at a direction determined based on the input; and
   (c) determining, by the at least one processor, an intersection of the ray in a three-dimensional space, the intersection indicating the position to place the orthodontic bracket with respect to the immersive photographic model, such that the determining step enables placement of the orthodontic bracket at the position on the patient's tooth; and
   (d) placing the orthodontic bracket on the patient's tooth at the indicated position.

2. The method of claim 1, further comprising superimposing a mark onto the immersive photographic model to illustrate to the health care professional the location selected for placement of the orthodontic bracket on the patient's tooth.

3. The method of claim 2, wherein said mark is a three-dimensional model of the orthodontic bracket.

4. The method of claim 3, further comprising positioning the three-dimensional model of the orthodontic bracket to appear to rest on the patient's tooth in one or more images rendered from one or more viewports of the immersive photographic model.

5. The method of claim 4, wherein the positioning the three-dimensional model of the orthodontic bracket comprises superimposing a simulated spacer onto the immersive photographic model, positioned between the model of the orthodontic bracket and the patient's tooth.

6. The method of claim 3, further comprising selecting the orthodontic bracket from a plurality of different types of orthodontic brackets, each type of orthodontic bracket designed for a different tooth anatomy or designed to achieve a different desired orthodontic goal.

7. The method of claim 2, further comprising scaling the mark to fit the dimensions of the patient's tooth based on dental measurements.

8. The method of claim 7, wherein the dental measurements are determined by one or more of the following:
   (i) analyzing an image that includes a measurement reading from a measurement tool;
   (ii) analyzing a size of the overlapping portions of images captured by nearby image sensors; and
   (iii) calculating the three-dimensional distance between the intersection and another intersection determined from another ray extended from another focal point of another viewport, the other ray directed based on another input.

9. The method of claim 1, further comprising, when a health care professional is placing the orthodontic bracket, superimposing a marking on an image of a patient's tooth at the position determined in (c) to guide the health care professional in placing the orthodontic bracket on the patient's tooth.

10. The method of claim 9, further comprising, when a health care professional is placing the orthodontic bracket, capturing, from an intraoral camera, a video including the image.

11. The method of claim 9, further comprising, when a health care professional is placing the orthodontic bracket:
   selecting one or more viewports corresponding to a perspective of the health care professional; and
   rendering the immersive photographic model to create the image of a patient's tooth used to superimpose the marking.

12. The method of claim 1, further comprising:
   once a health care professional has placed the orthodontic bracket on the patient's tooth, capturing an assessment image of the patient's tooth;
   determining where, in the assessment image, the orthodontic bracket is located;
   comparing the orthodontic bracket's determined location to the position to place the orthodontic bracket on the patient's tooth indicated in (c); and
   when the orthodontic bracket's determined location is determined not to correspond to the position indicated in (c), alerting the health care professional.

13. The method of claim 1, further comprising:
   receiving another input indicating another location selected by the health care professional on another image to indicate the position to place the orthodontic bracket on the patient's tooth, wherein the other image is rendered with respect to another viewport mapped onto the immersive photographic model of the patient's mouth; and extending another ray from the other viewport's focal point at a direction determined based on the other input, wherein determining (c) comprises determining the intersection in three-dimensional space between the ray extended in (b) and the other ray.

14. The method of claim 1, further comprising:

superimposing a generated three-dimensional model of the patient's tooth onto the immersive photographic model, wherein the determining (c) comprises determining the intersection between the ray and the three-dimensional model of the patient's tooth.

15. The method of claim 1, further comprising:

generating the immersive photographic model from data captured by a device for capturing imagery data of the interior of the patient's mouth, the device comprising:

a sphere including a plurality of pass-through surfaces or a dental tray adapted to at least partially enclose a dental arch of the patient, the tray including a plurality of pass-through surfaces; and a plurality of image sensors, each positioned to capture light transmitted through a pass-through surface in the plurality of pass-through surfaces and to record photographic images of the patient's mouth.

* * * * *

UNITED STATES PATENT AND TRADEMARK OFFICE
CERTIFICATE OF CORRECTION

PATENT NO. : 10,687,917 B2  
APPLICATION NO. : 15/650068  
DATED : June 23, 2020  
INVENTOR(S) : Elazar et al.

Page 1 of 1

It is certified that error appears in the above-identified patent and that said Letters Patent is hereby corrected as shown below:

In the Claims

Column 27, Claim 1, Line 53, replace "input; and" with --input;--.

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*